US011304989B2

(12) United States Patent
Kaempfer et al.

(10) Patent No.: US 11,304,989 B2
(45) Date of Patent: Apr. 19, 2022

(54) PEPTIDES FOR USE IN THE TREATMENT OF VIRAL INFECTIONS

(71) Applicant: Yissum Research Development Company of the Hebrew University of Jerusalem Ltd, Jerusalem (IL)

(72) Inventors: Raymond Kaempfer, Jerusalem (IL); Gila Arad, Mevasseret Zion (IL)

(73) Assignee: YISSUM RESEARCH DEVELOPMENT COMPANY OF THE HEBREW UNIVERSITY OF JERUSALEM LTD, Jerusalem (IL)

( * ) Notice: Subject to any disclaimer, the term of this patent is extended or adjusted under 35 U.S.C. 154(b) by 0 days.

(21) Appl. No.: 16/753,083

(22) PCT Filed: Oct. 2, 2018

(86) PCT No.: PCT/IL2018/051077
§ 371 (c)(1),
(2) Date: Apr. 2, 2020

(87) PCT Pub. No.: WO2019/069307
PCT Pub. Date: Apr. 11, 2019

(65) Prior Publication Data

US 2020/0276262 A1 Sep. 3, 2020

Related U.S. Application Data

(60) Provisional application No. 62/569,295, filed on Oct. 6, 2017.

(51) Int. Cl.
*A61K 38/08* (2019.01)
*A61K 31/215* (2006.01)
*A61K 31/351* (2006.01)
*A61K 45/06* (2006.01)
*A61P 31/16* (2006.01)

(52) U.S. Cl.
CPC .............. *A61K 38/08* (2013.01); *A61P 31/16* (2018.01); *A61K 31/215* (2013.01); *A61K 31/351* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 9,546,207 B2 * | 1/2017 | Kaempfer | ........ | C07K 14/70521 |
| 2005/0191296 A1 * | 9/2005 | Kaempfer | ........ | C07K 14/70521 424/144.1 |
| 2017/0189529 A1 | 7/2017 | Estelles et al. | | |

FOREIGN PATENT DOCUMENTS

| | | | |
|---|---|---|---|
| WO | 2004/087196 | A2 | 10/2004 |
| WO | 2013/108193 | A1 | 7/2013 |
| WO | 2015/083173 | A1 | 6/2015 |
| WO | WO 2015/083173 | * | 6/2015 |

OTHER PUBLICATIONS

Winquist et al. (Recommendations and Reports, Dec. 17, 1999 / 48(RR14);1-9) (Year: 1999).*
Smee et al. (Antivir Chem Chemother. 2006;17(4):185-92) (Year: 2006).*
Kobasa, D., et al., Enhanced virulence of influenza A viruses with the haemagglutinin of the 1918 pandemic virus, Nature 431, 703-707 (2004).
Oxford, J.S., Infuenza A pandemics of the 20th century with special reference to 1918: virology, pathology and epidemiology, Rev. Med. Virol. 10, 119-133 (2000).
Cheung, C.Y., et al., Induction of proinflammatory cytokines in human macrophages by influenza A (H5N1) viruses: a mechanism for the unusual severity of human disease?, Lancet 360, 1831-1837 (2002).
Peiris, J.S., et al., Re-emergence of fatal human influenza A subtype H5N1 disease, Lancet 363, 617-619 (2004).
Ramachandran, G., et al. , A peptide antagonist of CD28 signaling attenuates toxic shock and necrotizing soft-tissue infection induced by *Streptococcus pyogenes*, J. Infect. Dis. 211, 995-100 (2015).
Arad, G. et al., Binding of superantigen toxins into the CD28 homodimer interface is essential for induction of cytokine genes that mediate lethal shock, PLoS Biol. p. e1001149 (2011).
Evans, E.J., et al., Crystal structure of a soluble CD28-Fab complex, Nat. Immunol. 6, 271-279 (2005).
Tappe et al., Cytokine kinetics of Zika virus-infected patients from acute to reconvalescent phase, Med. Microbiol. Immunol. 205(3):269-273 (2016).
Levy, R., et al., Superantigens hyperinduce inflammatory cytokines by enhancing the B7-2/CD28 costimulatory receptor interaction, Proc. Natl. Acad. Sci. USA 113, E6437-E6446 (2016).
Barnard, D.L., et al., Effect of oral gavage treatment with ZnAL42 and other metallo-ion formulations on influenza A H5N1 and H1N1 virus infections in mice, Antivir. Chem. Chemother. 18, 125-132 (2007).
Nguyen, J.T., et al., Efficacy of Combined Therapy with Amantadine, Oseltamivir, and Ribavirin In Vivo against Susceptible and Amantadine-Resistant Influenza A Viruses, PLoS One 7, e31006 (2012).
Sidwell et al., Utilization of Pulse Oximetry for the Study of the Inhibitory Effects of Antiviral Agents on Influenza Virus in Mice, Antimicrob. Agents Chemother. 36, 473-476) (1992).
Sidwell, et al., Efficacy of Orally Administered T-705 on Lethal Avian Influenza A (H5N1) Virus Infections in Mice Antimicrob Agents Chemother 51:845-851 (2007).

(Continued)

*Primary Examiner* — Sergio Coffa
(74) *Attorney, Agent, or Firm* — Browdy and Neimark, PLLC

(57) ABSTRACT

Disclosed are peptides, compositions, combinations, kits and methods for the treatment of viral pathogen infection. Combinations and kits comprise the disclosed peptides together with an additional antiviral therapeutic agent.

8 Claims, 5 Drawing Sheets

Specification includes a Sequence Listing.

(56) References Cited

OTHER PUBLICATIONS

Ramachandran, CD28 Homodimer Interface Mimetic Peptide Acts as a Preventive and Therapeutic Agent in Models of Severe Bacterial Sepsis and Gram-Negative Bacterial Peritonitis, the Journal of Infetious Diseases, vol. 207, No. 12, pp. 1869-1877 (2013).
Osterholm, M.T., Preparing for the Next Pandemic, N. Engl. J. Med. 352, 1839-1842 (2005).

* cited by examiner

SEQUENCE LISTING

```
<160> NUMBER OF SEQ ID NOS: 11

<210> SEQ ID NO 1
<211> LENGTH: 202
<212> TYPE: PRT
<213> ORGANISM: Homo sapiens

<400> SEQUENCE: 1

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro Phe Trp Val Leu Val Val Val Gly Gly Val
    130                 135                 140

Leu Ala Cys Tyr Ser Leu Leu Val Thr Val Ala Phe Ile Ile Phe Trp
145                 150                 155                 160

Val Arg Ser Lys Arg Ser Arg Leu Leu His Ser Asp Tyr Met Asn Met
                165                 170                 175

Thr Pro Arg Arg Pro Gly Pro Thr Arg Lys His Tyr Gln Pro Tyr Ala
            180                 185                 190

Pro Pro Arg Asp Phe Ala Ala Tyr Arg Ser
        195                 200


<210> SEQ ID NO 2
<211> LENGTH: 8
<212> TYPE: PRT
<213> ORGANISM: Artificial Sequence
<220> FEATURE:
<223> OTHER INFORMATION: p2TA core sequence
<220> FEATURE:
<221> NAME/KEY: misc_feature
```

<223> OTHER INFORMATION: synthetic

<400> SEQUENCE: 2

Ser Pro Met Leu Val Ala Tyr Asp
1               5

<210> SEQ ID NO 3
<211> LENGTH: 9
<212> TYPE: PRT
<213> ORGANISM: Artificial Sequence
<220> FEATURE:
<223> OTHER INFORMATION: p1TA core sequence
<220> FEATURE:
<221> NAME/KEY: misc_feature
<223> OTHER INFORMATION: synthetic

<400> SEQUENCE: 3

His Val Lys Gly Lys His Leu Cys Pro
1               5

<210> SEQ ID NO 4
<211> LENGTH: 8
<212> TYPE: PRT
<213> ORGANISM: Artificial Sequence
<220> FEATURE:
<223> OTHER INFORMATION: p3TA core sequence
<220> FEATURE:
<221> NAME/KEY: misc_feature
<223> OTHER INFORMATION: synthetic

<400> SEQUENCE: 4

His Lys Gly Leu Asp Ser Ala Val
1               5

<210> SEQ ID NO 5
<211> LENGTH: 8
<212> TYPE: PRT
<213> ORGANISM: Artificial Sequence
<220> FEATURE:
<223> OTHER INFORMATION: p4TA core sequence
<220> FEATURE:
<221> NAME/KEY: misc_feature
<223> OTHER INFORMATION: synthetic

<400> SEQUENCE: 5

Tyr Val Asn Gln Thr Asp Ile Tyr
1               5

<210> SEQ ID NO 6
<211> LENGTH: 9
<212> TYPE: PRT
<213> ORGANISM: Artificial Sequence
<220> FEATURE:
<223> OTHER INFORMATION: p5TA core sequence
<220> FEATURE:
<221> NAME/KEY: misc_feature
<223> OTHER INFORMATION: synthetic

<400> SEQUENCE: 6

Ser Asn Gly Thr Ile Ile His Val Lys
1               5

<210> SEQ ID NO 7
<211> LENGTH: 10
<212> TYPE: PRT
<213> ORGANISM: Artificial Sequence
<220> FEATURE:
<223> OTHER INFORMATION: (D-A)-p2TA-(D-A)
<220> FEATURE:

<221> NAME/KEY: misc_feature
<223> OTHER INFORMATION: synthetic
<220> FEATURE:
<221> NAME/KEY: MISC_FEATURE
<222> LOCATION: (1)..(1)
<223> OTHER INFORMATION: X equals to D-Ala
<220> FEATURE:
<221> NAME/KEY: MISC_FEATURE
<222> LOCATION: (10)..(10)
<223> OTHER INFORMATION: X equals to D-Ala

<400> SEQUENCE: 7

Xaa Ser Pro Met Leu Val Ala Tyr Asp Xaa
1 5 10

<210> SEQ ID NO 8
<211> LENGTH: 11
<212> TYPE: PRT
<213> ORGANISM: Artificial Sequence
<220> FEATURE:
<223> OTHER INFORMATION: (D-A)-p1TA-(D-A)
<220> FEATURE:
<221> NAME/KEY: misc_feature
<223> OTHER INFORMATION: synthetic
<220> FEATURE:
<221> NAME/KEY: MISC_FEATURE
<222> LOCATION: (1)..(1)
<223> OTHER INFORMATION: X equals to D-Ala
<220> FEATURE:
<221> NAME/KEY: MISC_FEATURE
<222> LOCATION: (11)..(11)
<223> OTHER INFORMATION: X equals to D-Ala

<400> SEQUENCE: 8

Xaa His Val Lys Gly Lys His Leu Cys Pro Xaa
1 5 10

<210> SEQ ID NO 9
<211> LENGTH: 10
<212> TYPE: PRT
<213> ORGANISM: Artificial Sequence
<220> FEATURE:
<223> OTHER INFORMATION: (D-A)-p3TA-(D-A)
<220> FEATURE:
<221> NAME/KEY: misc_feature
<223> OTHER INFORMATION: synthetic
<220> FEATURE:
<221> NAME/KEY: MISC_FEATURE
<222> LOCATION: (1)..(1)
<223> OTHER INFORMATION: X equals to D-Ala
<220> FEATURE:
<221> NAME/KEY: MISC_FEATURE
<222> LOCATION: (10)..(10)
<223> OTHER INFORMATION: X equals to D-Ala

<400> SEQUENCE: 9

Xaa His Lys Gly Leu Asp Ser Ala Val Xaa
1 5 10

<210> SEQ ID NO 10
<211> LENGTH: 10
<212> TYPE: PRT
<213> ORGANISM: Artificial Sequence
<220> FEATURE:
<223> OTHER INFORMATION: (D-A)-p4TA-(D-A)
<220> FEATURE:
<221> NAME/KEY: misc_feature
<223> OTHER INFORMATION: synthetic
<220> FEATURE:
<221> NAME/KEY: MISC_FEATURE
<222> LOCATION: (1)..(1)
<223> OTHER INFORMATION: X equals to D-Ala
<220> FEATURE:

-continued

```
<221> NAME/KEY: MISC_FEATURE
<222> LOCATION: (10)..(10)
<223> OTHER INFORMATION: X equals to D-Ala

<400> SEQUENCE: 10

Xaa Tyr Val Asn Gln Thr Asp Ile Tyr Xaa
1               5                   10


<210> SEQ ID NO 11
<211> LENGTH: 11
<212> TYPE: PRT
<213> ORGANISM: Artificial Sequence
<220> FEATURE:
<223> OTHER INFORMATION: (D-A)-p5TA-(D-A)
<220> FEATURE:
<221> NAME/KEY: misc_feature
<223> OTHER INFORMATION: synthetic
<220> FEATURE:
<221> NAME/KEY: MISC_FEATURE
<222> LOCATION: (1)..(1)
<223> OTHER INFORMATION: X equals to D-Ala
<220> FEATURE:
<221> NAME/KEY: MISC_FEATURE
<222> LOCATION: (11)..(11)
<223> OTHER INFORMATION: X equals to D-Ala

<400> SEQUENCE: 11

Xaa Ser Asn Gly Thr Ile Ile His Val Lys Xaa
1               5                   10
```

PEPTIDES FOR USE IN THE TREATMENT OF VIRAL INFECTIONS

TECHNOLOGICAL FIELD

Disclosed are methods, compounds, combinations and uses thereof for treatment of infections caused by viral pathogens, including Orthomyxoviridae viruses, specifically influenza viruses Type A and Type B, Filoviridae or Flaviviridae viruses. The presently disclosed methods, compounds, combinations and uses in particular employ short peptides that specifically bind to CD28, and their synergistic combinations with antiviral agents.

BACKGROUND ART

References considered to be relevant as background to the presently disclosed subject matter are listed below:

[1] Osterholm, M. T. (2005) N. Engl. J. Med. 352, 1839-1842

[2] Kobasa, D., et al. (2004) Nature 431, 703-707

[3] Oxford, J. S., Rev. Med. Virol. 10, 119-133 (2000)

[4] Cheung, C. Y., et al. (2002) Lancet 360, 1831-1837

[5] Peiris, J. S., et al. (2004) Lancet 363, 617-619

[6] WO 2004/087196

[7] US 2017/0189529

[8] Ramachandran, G., et al. (2015) J. Infect. Dis. 211, 995-1003

[9] Arad, G. et al. (2011) PLoS Biol. page e1001149

[10] Evans, E. J., et al. (2005) Nat. Immunol. 6, 271-279

[11] Tappe et al. (2016) Med. Microbiol. Immunol. 205 (3):269-273

[12] Levy, R., et al. (2016) Proc. Natl. Acad. Sci. USA 113, E6437-E6446

[13] Barnard, D. L., et al. (2007) Antivir. Chem. Chemother. 18, 125-132

[14] Nguyen, J. T., et al. (2012) PLoS One 7, e31006

[15] Sidwell et al. (1992), Antimicrob. Agents Chemother. 36, 473-476)

[16] Sidwell, et al. Antimicrob Agents Chemother 51:845-851 (2007)

Acknowledgement of the above references herein is not to be inferred as meaning that these are in any way relevant to the patentability of the presently disclosed subject matter.

BACKGROUND

The inflammatory cytokine response is indispensable for protective immunity, yet viral infections often elicit an exaggerated response which is harmful to the host. Acute viral infections can lead to a cytokine storm, which is the excessive systemic expression of a healthy and vigorous immune system resulting in the release of multiple inflammatory mediators (cytokines, oxygen free radicals, and coagulation factors). Both pro-inflammatory cytokines (such as Tumor Necrosis Factor) and anti-inflammatory cytokines are elevated in the serum, and the fierce and often lethal interplay of these cytokines is referred to as a "cytokine storm". Primary contributors to the cytokine storm include Tumor Necrosis Factor-α (TNF-α), Interferon-γ, IL (interleukin)-2 and IL-6. The cytokine storm is an exaggerated immune response that is caused by rapidly proliferating and highly activated T-cells or natural killer (NK) cells. These cells are activated by infected macrophages. The cytokine storm must be treated and suppressed, to avoid a lethal result.

Acute respiratory viral infection (especially from the influenza A virus H5N1 subtype) results in a cytokine storm [1] affecting the lungs, and can be lethal. Avian influenza H5N1 was first isolated from birds in South Africa in 1961, is extremely contagious and can be deadly to domesticated poultry as well as to humans. Since January 2003, outbreaks of H5N1 have caused incidences of avian and human infection in several countries around the world. Infections in humans coincided with devastating epidemics in poultry farms in Asian countries, with a reported mortality rate approaching 100%. H5N1 influenza virus is endemic in Asian domestic fowl, and unlikely to be eradicated.

It is believed that cytokine storm was responsible for many of the deaths during the 1918 Influenza A pandemic, which killed a disproportionate number of young adults, estimated to be 40-50 million people. This has been indicated as the probable reason of many deaths during the SARS epidemic in 2003, in Hong Kong. Human death from the bird flu virus usually involve cytokine storms. Avian influenza type A subtype H5N1 ("bird flu") infected patients die from acute respiratory distress syndrome (ARDS) caused by the cytokine storm, and not directly from the virus infection. Death will usually result from multi-organ system failure, and not only from lung failure.

The hemagglutinin of the Influenza A virus that caused the 1918 pandemic confers enhanced pathogenicity in mice when compared to recent viruses that are otherwise nonpathogenic in humans. Highly virulent recombinant viruses expressing the 1918 viral hemagglutinin could infect the entire lung and induce high levels of macrophage-derived chemokines and cytokines, resulting in infiltration of inflammatory cells and severe haemorrhage [2], hallmarks of the illness produced during the original pandemic [3].

Until around 1997, swine influenza strains were almost exclusively H1N1. Between 1997 and 2002, new strains of three different subtypes and five different genotypes emerged as causes of influenza among pigs, H3N2, a reassortant from human, swine and avian viruses, reassortment between H1N1 and H3N2 produced H1N2, and a rare Canadian strain H4N6 crossed species barrier from birds to pigs. The global 2009 flu pandemic was an outbreak of a new strain of influenza A virus subtype H1N1 (Pandemic H1N1/09), which is a reassortant from five known strains of influenza A virus, one endemic in humans, two endemic in birds and the other two endemic in pigs. Patients becoming severely ill are treated with antiviral drugs such as Oseltamivir (Tamiflu®) and Zanamivir (Relenza®), but were not always free from side effects. The H1N1 pandemic is being controlled by severe measures. Patients with H5N1 disease in 2003 had unusually high serum concentrations of chemokines (e.g., interferon-γ induced protein-10 (IP-10), also named C-X-C motif chemokine 10 (CXCL10), a chemokine induced by Interferon-γ). Taken together with the observation that H5N1 influenza viruses induce high levels of proinflammatory cytokines from macrophage cultures in vitro [4], these findings suggested that the cytokine storm also contributes to the pathogenesis of H5N1 disease [5].

While the importance of establishing a reliable prophylactic and/or therapeutic treatment for not only sporadic outbreaks of H5N1, H1N1 and other influenza virus infections in humans, but also for use in the event that pandemic situation arises, is evident, effective vaccines are rare. For example, there is no available effective vaccine against H5N1 for use in humans, and according to the World Health Organization (WHO), vaccines developed against the 2003 strain of H5N1 are not protective against the 2004 Vietnam H5N1 strain, which has mutated (due to antigenic drift)

significantly. Moreover, producing a vaccine against a pandemic bird flu strain, using currently available technologies would take at least six months after the pandemic starts and thus would not be readily available. Furthermore, even then, the supply would probably only be large enough to vaccinate 14% of the global population [3]. Preventing a pandemic by way of vaccination may not be reliable means for control of viruses of the Orthomyxoviridae family, particularly of Influenza virus A family, largely due to the short time period between strain detection and need for the product. The development of broad-spectrum means to control such viral infections, and particularly influenza A infections, and thus attenuate and inhibit resulting cytokine storm resulting by the viral infection associated therewith, in the form of safe and effective anti-viral therapy is desired. At present, there are two classes of drugs commercially available for the prevention and treatment of influenza virus infections in humans, M2 ion channel blockers and neuraminidase inhibitors.

Amantadine and Rimantadine function by blocking the ion channel activity of a viral protein, which is mainly required during virus entry into the host cells in the early phase of the replication life cycle. Both treatments are highly effective in treating influenza A, but cause significant side effects on the central nervous system, liver and kidneys. M2 inhibitor-resistant influenza viruses are generated in up to 30% of patients, and these viruses are virulent and transmissible. Neuraminidase inhibitors (e.g. Oseltamivir—Tamiflu®, Roche; Zanamivir—Relenza®, Biota/GlaxoSmithKline) are used to prevent the release of the newly formed virus from infected cells and spread within the host. Both drugs efficiently inhibited non-avian derived influenza viruses in clinical studies, however escape from the selective pressures of neuraminidase inhibitors has been observed in cell culture as well as in patients. Oseltamivir (Tamiflu®, Roche), Peramivir (Rapivab®) or Zanamivir (Relenza®) are chemically related drugs that are among the main line of therapy proposed for treatment of the H5N1 Avian influenza in humans. Other antiviral drugs that are active against influenza A viruses include amantadine and rimantadine (known as adamantanes, serving as M2 proton channel blockers) and favipravir (polymerase inhibitor) and laninamivir. These antiviral drugs do not address the lethal cytokine storm associated with the infection. Oseltamivir and Zanamivir are also used for treatment of swine flu-infected patients.

Overall, many of current anti-viral therapies are directed towards targeting viral components, and are therefore prone to compensatory viral escape mechanisms. For example, a recent report suggested that two Vietnamese patients treated with Tamiflu® were resistant to the drug and died from avian influenza. This again indicates the need for alternative therapy options.

Methods and compositions based on immunomodulatory peptides for inhibition of activation of a T cell costimulatory pathway (CD28/B7) consequently preventing cytokine storm were previously demonstrated [6]. Combination of an antibody directed to influenza virus with host-cell targeting therapeutic for the treatment and prophylaxis of influenza virus infection was described in [7].

SUMMARY

In a first aspect of the present disclosure, disclosed herein is a method for the treatment of a viral pathogen infection in a subject in need of such treatment, the method comprising the step of administering to said subject a therapeutically effective amount of at least one isolated peptide which specifically binds to the crystallographic homodimer interface of CD28 with a binding affinity characterized by a $K_D$ of from about 0.1 to 30 micromolar or functional derivative of said peptide having the same binding affinity, or a composition comprising said at least one isolated peptide or functional derivative thereof, said method further optionally comprising a step of administering to said subject at least one additional antiviral therapeutic agent.

In all aspects and embodiments of the present disclosure, the treatment of said viral infection controls and/or attenuates and/or inhibits a cytokine storm induced by said viral pathogen. More specifically, said treatment prevents worsening, arrests and/or ameliorates at least one symptom of said viral infection or damage to said subject or an organ or tissue of said subject, emanating from or associated with said viral infection.

The symptom or damage emanating from or associated with said viral infection can be, but are not limited to, at least one of fever (body temperature of >38° C.), acute respiratory distress syndrome (ARDS), multiple organ dysfunction syndrome (MODS), systemic inflammatory response syndrome (SIRS), hypotension, tachycardia, dyspnea, ischemia, insufficient tissue perfusion (especially involving the major organs), uncontrollable hemorrhage, multisystem organ failure (primarily due to hypoxia or tissue acidosis) or severe metabolism dysregulation. Some nonlimiting examples of fever are Zika fever, West Nile fever, Dengue fever or Yellow fever. In specific embodiments, said treatment prevents death of said subject.

In all aspects and embodiments of the present disclosure, said viral pathogen can be, but is not limited to a virus of any one of the Orthomyxoviridae, Filoviridae, Flaviviridae, Coronaviridae or Poxviridae families.

Thus, a virus of the Orthomyxoviridae family can be, but is not limited to any one of Influenza virus type A, Influenza virus type B or Influenza virus type C or any subtype or reassortant thereof. In some specific embodiments, an avian Influenza type A virus or any subtype or reassortant thereof can have, a haemagglutinin component (HA) of subtype H5, H7 or H9, but is not limited thereto, and a neuraminidase component (NA) of subtypes 1 or 2, but is not limited thereto. A specific nonlimiting example of avian Influenza virus type A is the subtype H5N1. Influenza virus type A can also be, for example, swine Influenza type A virus. A specific nonlimiting example is swine Influenza type A subtype H1N1.

In other embodiments, the viral pathogen can be a virus of the Filoviridae family, for example, Marburg virus (MARV) or Ebola virus (EBOV), but not limited thereto. In other embodiments, said viral pathogen can be a virus of the Flaviviridae family, for example Zika virus (ZIKV), West Nile virus (WNV), Dengue virus (DENV) or Yellow Fever virus (YFV), but is not limited thereto. In yet other embodiments, said viral pathogen can be a virus of the Coronaviridae, for example Severe Acute Respiratory Syndrome virus (SARS-CoV), but not limited thereto.

In all aspects and embodiments of the present disclosure, the said at least one isolated peptide can be, but is not limited to, any one of a peptide consisting of the amino acid sequence SPMLVAYD as denoted by SEQ ID NO. 2, also termed herein p2TA core sequence; a peptide consisting of the amino acid sequence HVKGKHLCP as denoted by SEQ ID NO. 3, also termed herein p1TA core sequence; a peptide consisting of the amino acid sequence HKGLDSAV as denoted by SEQ ID NO. 4, also termed herein p3TA core sequence, a peptide consisting of the amino acid sequence YVNQTDIY as denoted by SEQ ID NO. 5, also termed herein p4TA core sequence; or a peptide consisting of the amino acid sequence SNGTIIHVK as denoted by SEQ ID NO. 6, also termed herein p5TA core sequence, and functional derivatives thereof having the same binding affinity to the crystallographic homodimer interface of CD28, or pharmaceutically acceptable salts and esters thereof.

In embodiments of the present disclosure, the said at least one isolated peptide can be:

(a) a peptide which is at least 80% homologous to a peptide as defined above;

(b) a peptide as defined in claim 14 extended by 1-3 consecutive amino acid residues present in corresponding adjacent positions of the amino acid sequence of SEQ ID NO. 1;

(c) a peptide as defined above, or as defined in (a) or (b) above, that is extended at the N terminus and/or the C terminus:

(i) by a lauryl cysteine at the N terminus and a cysteine at the C terminus; or (ii) by an organic moiety that is not a naturally occurring or synthetic amino acid residue; or (iii) by identical hydrophobic amino acid residue(s) which may be naturally occurring or synthetic amino acid residues;

(iv) by a palmitoyl-lysine tail, wherein said tail is at the N terminus; or (d) a dimer or multimer of a peptide as defined above or the resulting peptide of any of (a), (b) or (c) above;

wherein the resultant peptide of any of (a), (b), (c) or (d) maintains the ability to specifically bind to the said human CD28 homodimer interface at a binding affinity characterized by $K_D$ of lower than 30 micromolar, more specifically $K_D$ of from about 0.1 to about 30 micromolar, and of achieving a therapeutic effect in the treatment of a viral pathogen infection.

In specific embodiments, said isolated peptide as defined above is extended at the N-terminus and/or C-terminus thereof with D-alanine.

A specific example of a peptide as defined herein is an isolated peptide that has the amino acid sequence SPMLVAYD as denoted by SEQ ID NO. 2, also termed herein "p2TA core sequence", or the amino acid sequence (D-Ala)-SPMLVAYD-(D-Ala) denoted by SEQ ID NO. 7, also termed herein (D-Ala)-p2TA-(D-Ala), or a pharmaceutically acceptable salt thereof, for example its sodium salt.

In a second aspect, the present disclosure provides for a method of treatment for the treatment of a viral pathogen infection in a subject in need of such treatment, the method comprising the step of administering to said subject a therapeutically effective amount of at least one isolated peptide which specifically binds to the crystallographic homodimer interface of CD28 with a binding affinity characterized by a $K_D$ of from about 0.1 to 30 micromolar or functional derivative of said peptide having the same binding affinity, or a composition comprising said at least one isolated peptide or functional derivative thereof, and further comprising a step of administering to said subject at least one additional antiviral therapeutic agent.

In all embodiments of this second aspect of the said treatment, the said damage or symptom emanating from or associated with said viral infection, the said viral pathogen and the said isolated peptides can be as specifically defined above.

In embodiments of the present disclosure, the said additional antiviral therapeutic agent is other than an antibody directed against said viral pathogen.

In all aspects and embodiments of the present disclosure, the said at least one additional antiviral therapeutic agent can be any one of a viral neuraminidase inhibitor, a viral polymerase inhibitor and an M2 ion-channel blocker. Non-limiting examples of neuraminidase se inhibitor are Oseltamivir or Zanamivir.

In aspects and embodiments of the present disclosure, the at least one additional antiviral therapeutic agent can be administered to said subject at either a suboptimal dose or at a therapeutic dose.

In aspects and embodiments of the present disclosure, each said at least one isolated peptide or composition comprising the same or said at least one additional antiviral agent can be administered to said subject by a route selected from the group consisting of intravenous, intramuscular or intraperitoneal administration, intrathecal or subcutaneous injection, oral, intrarectal, intranasal, ocular and topical administration.

In all aspects and embodiments of the present disclosure, said subject in need is a human subject.

In aspects and embodiments of the present disclosure, said isolated peptide is administered to said human subject at an amount of from about 0.05 mg to about 0.5 mg peptide/kg body weight of said subject.

In aspects and embodiments of the present disclosure, the said at least one isolated peptide and said at least one additional antiviral therapeutic agent can be administered to said subject simultaneously. Alternatively, said at least one isolated peptide and said at least one additional antiviral therapeutic agent can be administered to said subject at different time points, at different intervals between administrations, for different treatment periods, and/or at any order of administration. Each of said isolated peptide or composition comprising the same and said additional antiviral therapeutic agent can be administered to said subject at one or more identical or different treatment periods of one or more weeks of once daily, once every three days, once every five days or once weekly administrations of each of said isolated peptide and said additional antiviral agent, said treatment periods being consecutive or are set apart from each other by non-treatment intervals of 1 or several days or 1 or several weeks. The said interval between administration of said at least one isolated peptide and said at least one additional antiviral therapeutic agent can be, for example, between about 5 minutes to about 5 hours.

In aspects and embodiments of the present disclosure, each of said isolated peptide or composition comprising the same and said additional antiviral agent can be administered to said subject immediately following, or within from about 30 minutes up to about 10 days following exposure to the virus, whether before or after manifestation of clinical symptoms/damage.

In all aspects and embodiments of the present disclosure, said composition comprising said at least isolated peptide or functional derivative or pharmaceutically acceptable salt or ester thereof can comprise at least one of pharmaceutically acceptable additives, carriers, diluents and excipients.

Also disclosed herein is least one isolated peptide which specifically binds to the crystallographic homodimer interface of CD28 with a binding affinity characterized by a $K_D$ of from about 0.1 to 30 micromolar or functional derivative of said peptide having the same binding affinity, or a composition comprising said at least one isolated peptide or functional derivative thereof, for use in a method for treatment of a viral pathogen infection in a subject in need of such treatment, said method further optionally comprising administering to said subject at least one additional antiviral therapeutic agent.

In yet a third aspect of the present disclosure, disclosed is a combination, particularly a therapeutic combination, comprising at least one isolated peptide which specifically binds to the crystallographic homodimer interface of CD28 with a binding affinity characterized by a $K_D$ of from about 0.1 to 30 micromolar or functional derivative of said peptide having the same binding affinity and at least one additional antiviral therapeutic agent.

Also in this aspect of the present disclosure and embodiments thereof, the said isolated peptide can be an isolated peptide as defined for any of the aspects and embodiments described above. In specific embodiments, the said isolated peptide has the amino acid sequence SPMLVAYD as denoted by SEQ ID NO. 2, also termed herein p2TA core sequence, or the amino acid sequence (D-Ala)-SPMLVAYD-(D-Ala) denoted by SEQ ID NO. 7, also termed herein (D-Ala)-p2TA-(D-Ala), or pharmaceutically acceptable salts and esters thereof, for example the sodium salt thereof.

In some embodiments, the said additional antiviral therapeutic agent comprised in said combination can be a viral neuraminidase inhibitor, a viral polymerase inhibitor or an M2 ion-channel blocker. Nonlimiting examples of neuraminidase inhibitors are Oseltamivir or Zanamivir. In some embodiments, the said at least one additional antiviral therapeutic agent comprised in said combination is other than an antibody directed against said viral pathogen.

The said combination can be used in the treatment of a viral pathogen infection in a subject in need of such treatment, wherein "treatment" is as defined above.

In a further, fourth aspect of the present disclosure, there is provided a kit for the treatment of a viral pathogen infection and/or at least one symptom thereof in a human subject in need of such treatment, comprising:

(a) at least one isolated peptide which specifically binds to the crystallographic homodimer interface of CD28 with a binding affinity characterized by a $K_D$ of from about 0.1 to 30 micromolar, optionally comprised in a composition further comprising a pharmaceutically acceptable carrier or diluent, optionally in a first dosage unit form;

(b) an additional antiviral therapeutic agent, optionally comprised in a composition further comprising a pharmaceutically acceptable carrier or diluent, optionally in a second dosage unit form;

(c) container means for containing said first and second dosage forms jointly or separately;

(d) instructions for use; and optionally (e) means for administering said at least one isolated peptide and said at least one additional antiviral therapeutic agent to said subject.

In the disclosed kit, the said isolated peptide can be an isolated peptide as defined above. In specific embodiments of the disclosed kit, said isolated peptide has the amino acid sequence SPMLVAYD as denoted by SEQ ID NO. 2, also termed herein p2TA core sequence, or the amino acid sequence (D-Ala)-SPMLVAYD-(D-Ala) denoted by SEQ ID NO. 7, also termed herein (D-Ala)-p2TA-(D-Ala), or pharmaceutically acceptable salts and esters thereof, for example the sodium salt thereof.

In embodiments of the disclosed kit, said additional antiviral therapeutic agent is a viral neuraminidase inhibitor, a viral polymerase inhibitor or an M2 ion-channel blocker. Specific neuraminidase inhibitors can be, but are not limited to Oseltamivir or Zanamivir. In other embodiments of the disclosed kit, said additional antiviral therapeutic agent is other than an antibody directed against said viral pathogen.

The disclosed kit can be designed for use in the treatment of a viral pathogen infection in a subject in need of such treatment.

Figure 1A:
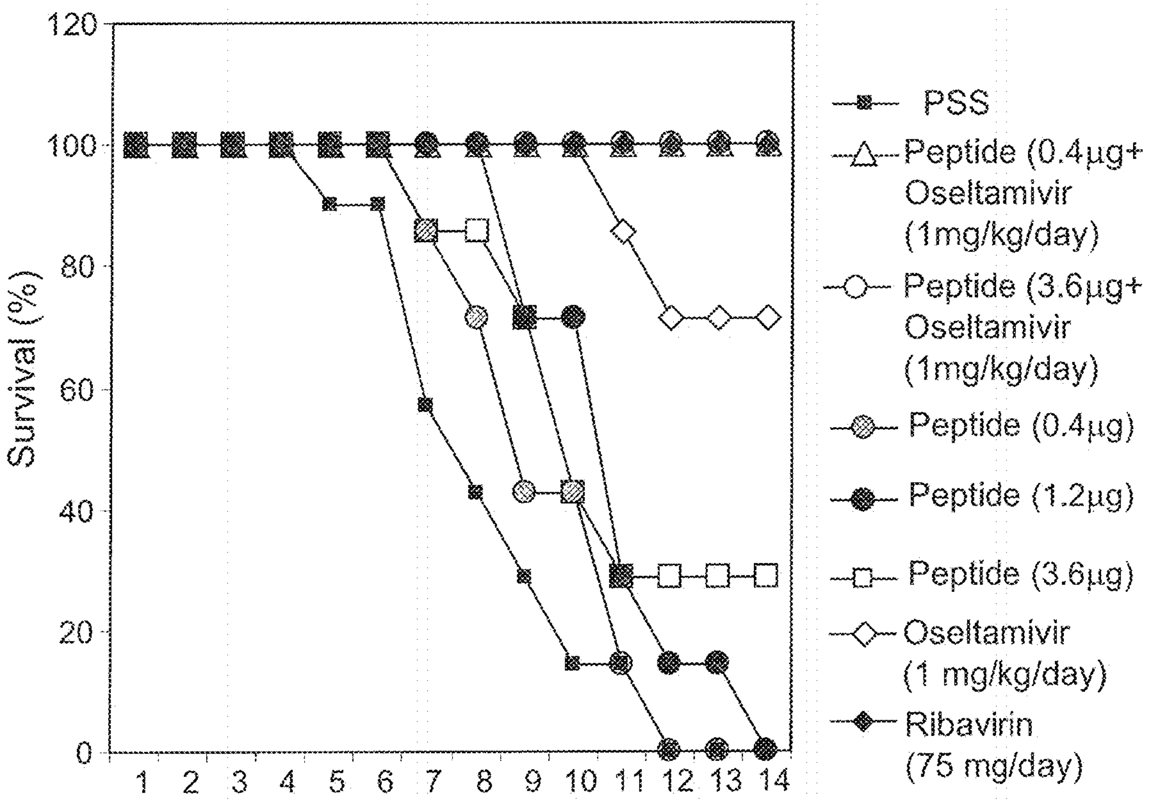
FIG. 1A-1B: The p2TA Peptide protects mice from lethal avian influenza infection.
Figure 1B:
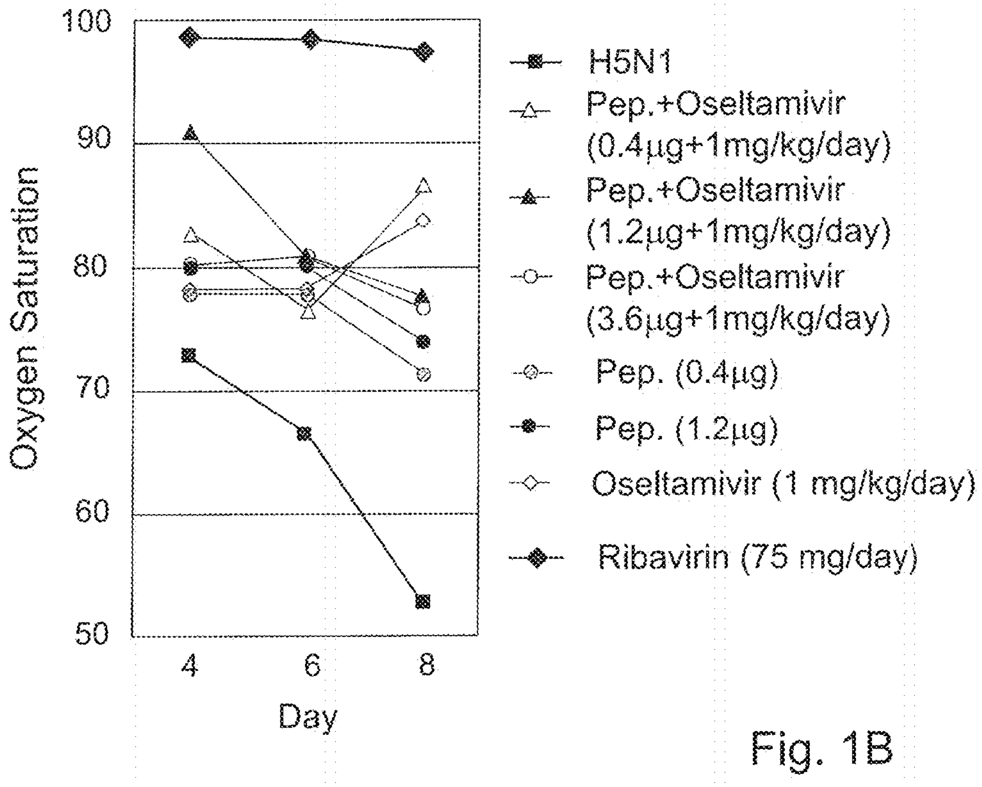

Balb/c mice (n=10/group) were infected both per os and intraperitoneally (i.p.) with influenza A H5N1 Duck/MN/1525/81 virus at 1:400 dilution (LD about $1\times10^5$). Treatment with p2TA peptide, also denoted by SEQ ID NO: 7, intraperitoneally (i.p.), Oseltamivir (per os) or Ribavirin (i.p.) was bi-daily for 5 days, 8 hours apart, to total daily doses as shown. PSS, untreated. Survival (FIG. 1A) was monitored during up to 21 days (only the first 14 days are shown) and remained constant after day 13 except for the Ribavirin group where one mouse died on day 16. Oxygen saturation was measured on days 4-8 (FIG. 1B). Body weights were measured from day 0; histology was performed on days 6 and 21 on additional animals in each group (not shown). Abbreviations: Pep, peptide.

FIG. 2A-2D: The p2TA peptide protects mice from lethal H1N1 and H5N1 influenza infection and synergizes with Oseltamivir.

Survival was monitored in infected BALB/c mice. Treatment with half the daily dose was done twice a day during 5 days post infection. p2TA was administered i.p., at the indicated daily dose per mouse (μg). Control, no peptide. Oseltamivir (Osel) was administered per os, at the indicated daily dose (mg/kg). As positive control served ribavirin. Kaplan-Meier survival curves of various groups are shown. A log-rank (Mantel-Cox) test was performed to compare survival between groups. *$p<0.05$, *$p<0.001$, **$p<0.0001$.

Figures 2A, 2B, 2C, 2D:
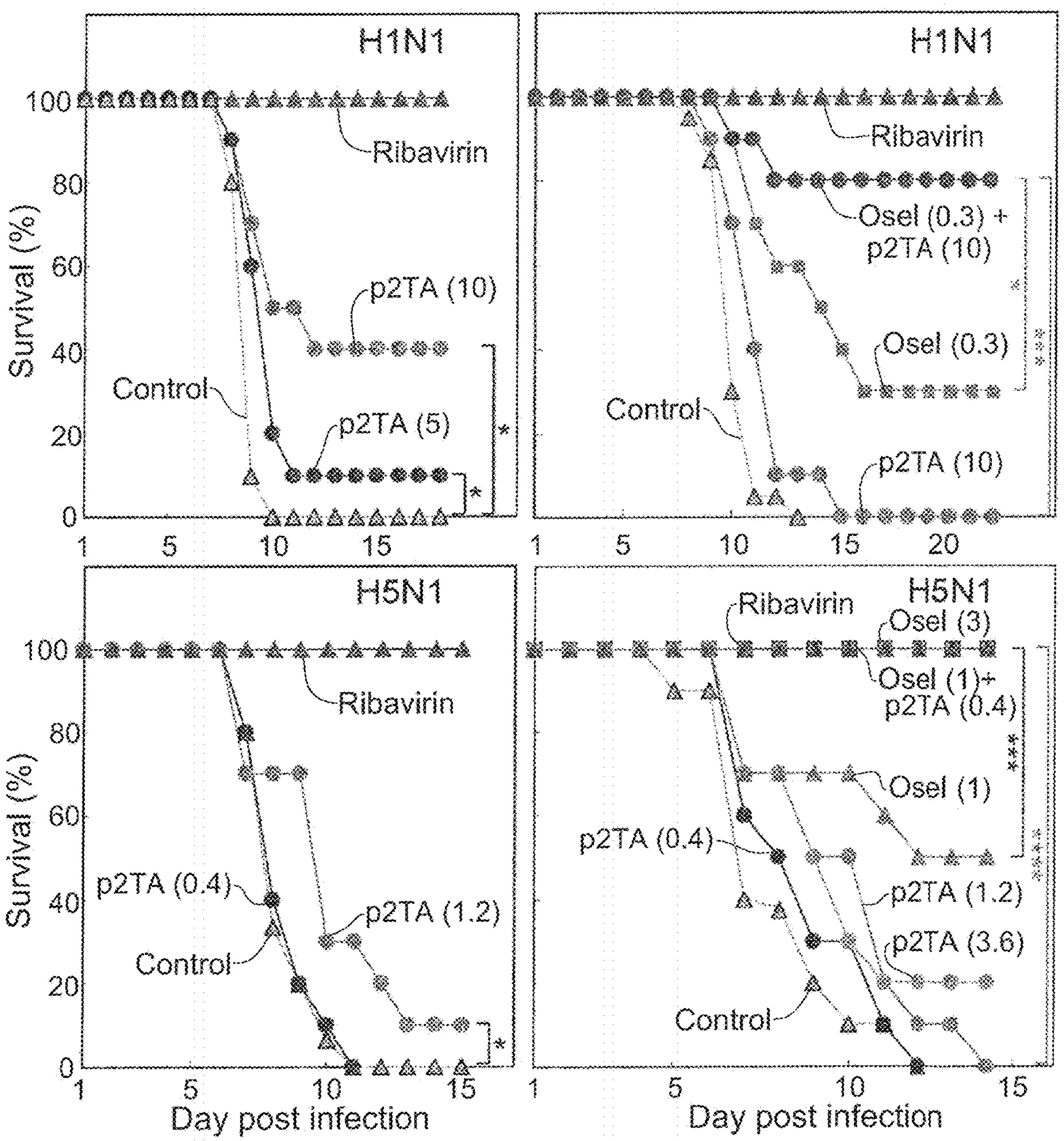

FIG. 2A: Survival curves showing a dose-dependent protection from lethal pandemic H1N1/A/California/04/09 influenza infection by p2TA. H1N1 virus (3 LD50) was administered intranasally.

FIG. 2B: Survival curves demonstrating that p2TA and Oseltamivir synergize in protecting mice from lethal H1N1/A/California/04/09 influenza infection.

FIG. 2C: Survival curves showing a dose-dependent protection from lethal H5N1/Duck/MN/1525/81 influenza infection by p2TA. H5N1 virus, 1:400 diluted (LD100~$1\times10^5$), was administered intranasally.

FIG. 2D: Survival curves showing dose-dependent protection by p2TA from lethal H5N1/Duck/MN/1525/81 influenza infection. p2TA and Oseltamivir synergize in protecting mice from lethal H5N1 influenza infection.

Figure 3A:
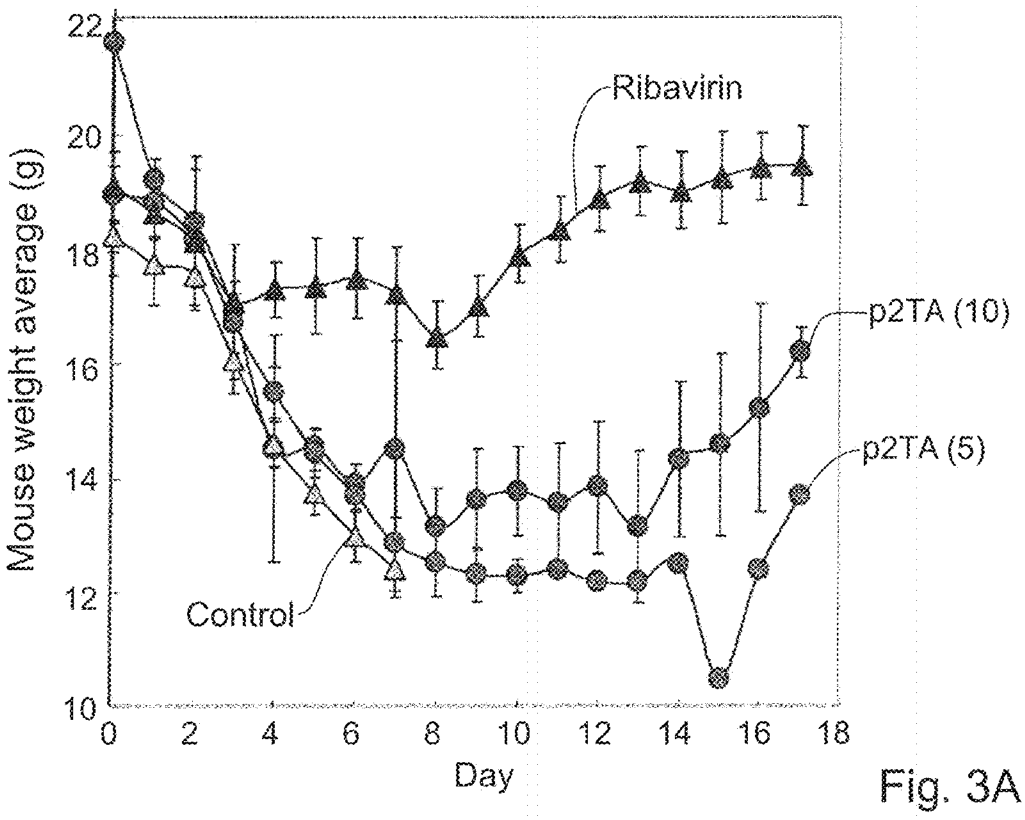
Figure 3B:
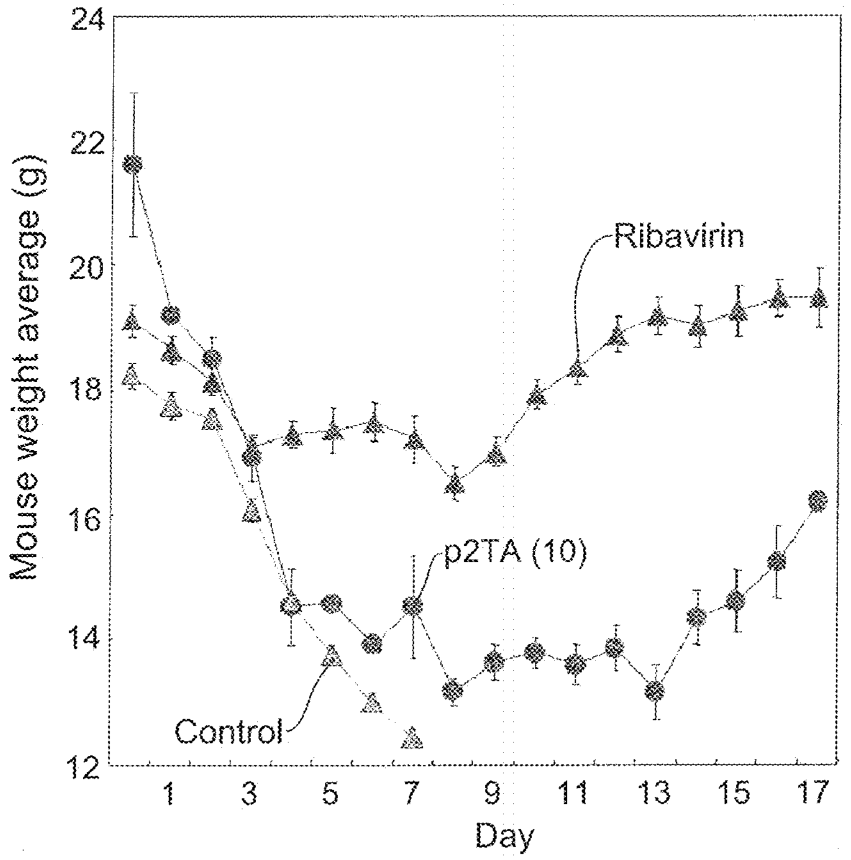

FIG. 3A-FIG. 3B: Weight recovery in mice protected by the p2TA peptide from lethal pandemic H1N1/A/California/04/09 influenza infection.

FIG. 3A: Graph showing weights (means ±SD) determined daily for mice participating in the experiment described in FIG. 2A. The p2TA peptide was administered intraperitoneally at the indicated doses per mouse (μg). As a positive control served Ribavirin, administered intraperitoneally (75 mg/kg). FIG. 3B: Graph showing weights determined daily for mice in the experiment of FIG. 2A (means±SEM, n>4). p2TA was administered at a daily dose of 10 μg per mouse. As positive control served ribavirin.

FIG. 4A-4D: The p2TA peptide improves arterial oxygen saturation in mice lethally infected with H5N1 influenza virus and attenuates inflammatory cytokine expression in lungs.

Figure 4B:
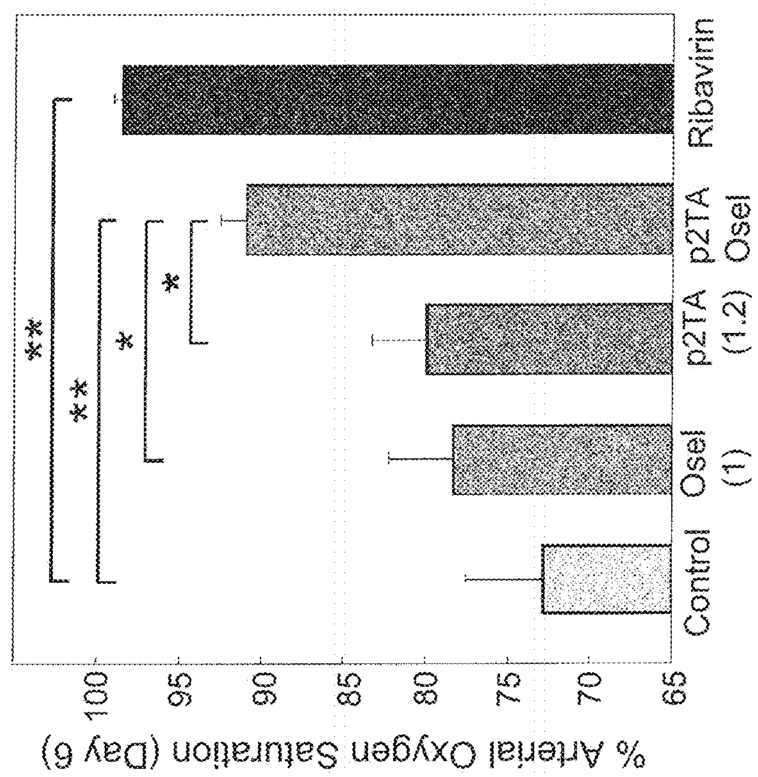
Figure 4A:
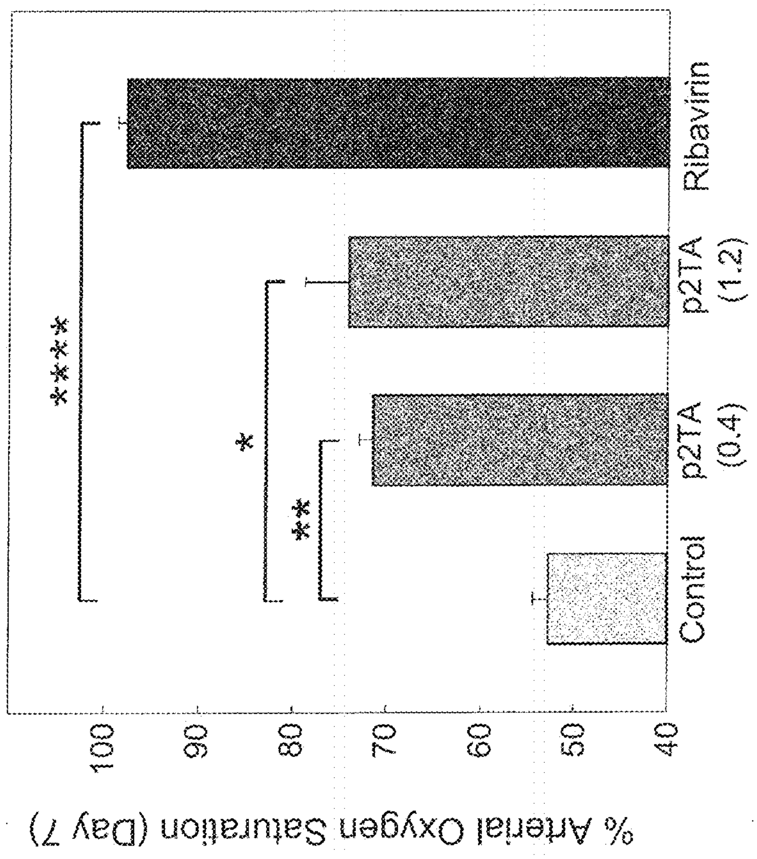

FIG. 4A: Arterial oxygen saturation determined on day 7 for mice infected with H5N1 influenza virus in the experiment of FIG. 2C.

FIG. 4B: Arterial oxygen saturation determined on day 6 for mice in the experiment of FIG. 2D.

Means+SEM; n=5. Mice received p2TA at the indicated daily dose per mouse (μg), Oseltamivir (Osel) at 1 mg/kg, or both (p2TA/Osel). As positive control served ribavirin. Single and combined treatments were compared using two-tailed unpaired Student's t-test; *p<0.05, p<0.05, **p<0.0001.

Figure 4C:
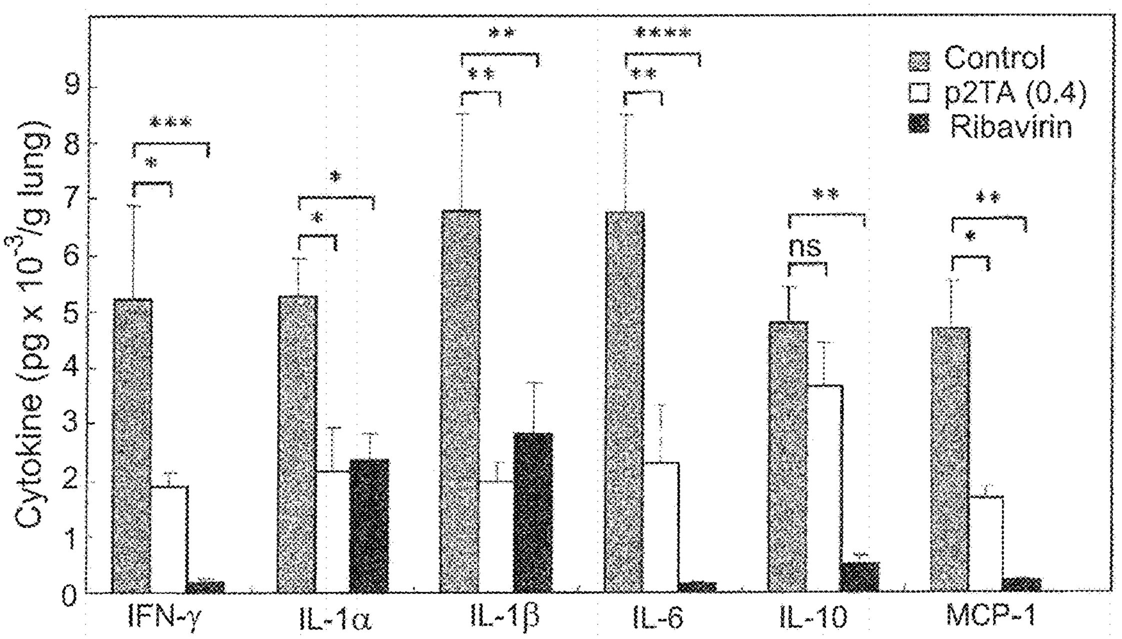

FIG. 4C: Cytokine and chemokine levels in lungs of mice infected with H5N1 influenza virus in FIG. 2D, sacrificed on day 6 post infection. To allow presentation on a common y-axis, assay values were divided by 6 for IFN-γ, by 5 for IL-6, by 20 for MCP-1, and multiplied by 4 for IL-10 (means±SEM, n=5). Treatments were compared using one-way analysis of variance followed by Dunnett's multiple comparisons test; *p<0.05, p<0.005, *p<0.001, ****p<0.0001.

Figure 4D:
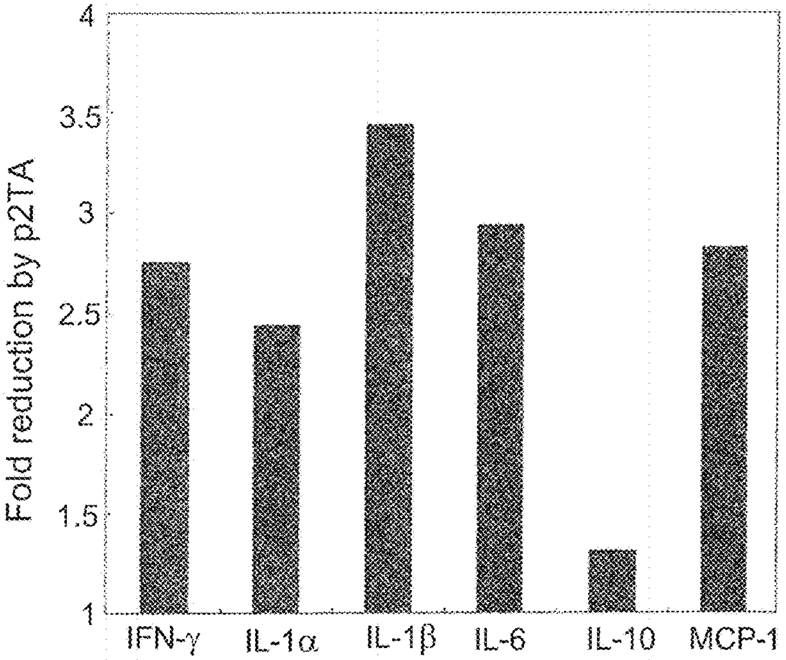

FIG. 4D: A bar graph showing that p2TA selectively attenuates expression of inflammatory mediators in lungs of mice infected with H5N1/Duck/MN/1525/81 influenza virus. Cytokine and chemokine levels in lungs of mice infected with H5N1 influenza virus, sacrificed on day 6 post infection. Fold reduction by p2TA is plotted for the data in FIG. 4C.

DETAILED DESCRIPTION OF EMBODIMENTS

As indicated above, cytokine storm (hypercytokinemia) is the systemic expression of a healthy and vigorous immune system resulting in the release of more than 150 inflammatory mediators (cytokines, oxygen free radicals, and coagulation factors). Both Th1 pro-inflammatory cytokines and Th2 anti-inflammatory cytokines are elevated in the serum of patients experiencing a cytokine storm. Cytokine storms potentially damage body tissues and organs, may result in death, and can occur in a number of infectious diseases including avian influenza and swine influenza.

It is suggested that treatment aimed at manipulating the host immune system to interfere with the cytokine storm initiated by activation of host's pro-inflammatory Th1 cells and monocytes by a viral pathogen, has a significant potential to control, attenuate, inhibit and prevent cytokine storm associated conditions without imposing on the virus itself selective pressure to mutate in a compensatory manner.

The present inventors have previously described various human CD28 mimetic peptides, that specifically bind to CD28 at a binding affinity characterized by $K_D$ lower than 30 micromolar, more specifically $K_D$ between about 0.1 and 30 micromolar [8] and exhibit immunomodulatory activity.

The results presented in the following Examples show that such peptides that specifically bind to the crystallographic homodimer interface of CD28 (also referred to as "short peptides defined herein" or "peptides defined herein" or "present peptides"), can be effectively used for treating viral pathogen infections, and control, attenuate and/or inhibit cytokine storm induced/caused by the infecting viral pathogen. The results further show a synergistic effect of treatment with peptides as defined herein in combination with other, additional therapeutic antiviral agent/s.

According to a first aspect of the present disclosure, disclosed herein is a method for the treatment of a viral pathogen infection in a subject in need of such treatment. The disclosed method of this first aspect of the disclosure comprises the step of administering to a subject a therapeutically effective amount of at least one isolated peptide or as defined herein, or of a composition comprising said at least one isolated peptide. This treatment led to control and inhibition of cytokine storm emanating from the viral pathogen infection, and prevented or delayed death of virally infected animals.

In other words the present disclosure provides a method for the treatment of a viral pathogen infection in a subject in need of such treatment, said method comprising the step of administering to said subject a therapeutically effective amount of at least one isolated peptide which specifically binds to the crystallographic homodimer interface of CD28 with a binding affinity characterized by a $K_D$ of from about 0.1 to 30 micromolar or functional derivative of said peptide having the same binding affinity, or a composition comprising said at least one isolated peptide or functional derivative thereof.

According to a second aspect, disclosed herein is a method for the treatment of a viral pathogen infection in a subject in need of such treatment, comprising administering to a subject a therapeutically effective amount of at least one isolated peptide as defined herein, or of a composition comprising said at least isolated one peptide, and another, additional antiviral therapeutic agent. As shown in the following Examples, treatment with both a peptide as defined herein and an antiviral drug exhibited a synergistic effect in control and inhibition of cytokine storm emanating from the viral pathogen infection, and protected infected animals from death.

Therefore the present disclosure further provides a method for the treatment of a viral pathogen infection in a subject in need of such treatment, said method comprising the step of administering to said subject a therapeutically effective amount of at least one isolated peptide which specifically binds to the crystallographic homodimer interface of CD28 with a binding affinity characterized by a $K_D$ of from about 0.1 to 30 micromolar or functional derivative of said peptide having the same binding affinity, or a composition comprising said at least one isolated peptide or functional derivative thereof, said method further comprising a step of administering to said subject at least one additional antiviral therapeutic agent.

By the term "additional antiviral therapeutic agent" (or "drug") as used herein is meant that the additional antiviral therapeutic agent/drug (which per se exhibits antiviral activity) is other than the peptide/s as defined herein.

In the above and other embodiments, the treatment as herein defined controls and/or attenuates and/or inhibits a cytokine storm induced by said viral pathogen.

The method of treatment as herein defined prevents the progression of said viral infection and ultimately prevents death of the subject.

In embodiments of the methods of these first and second aspects of the present disclosure, said treatment prevents worsening, arrests and/or ameliorates at least one symptom of the viral infection or damage to said subject or an organ or tissue of said subject, emanating from or associated with said viral infection. The said symptom of the viral infection or said damage can be at least one of fever (temperature of >38° C.), acute respiratory distress syndrome (ARDS), multiple organ dysfunction syndrome (MODS), systemic inflammatory response syndrome (SIRS), hypotension, tachycardia, dyspnea, ischemia, insufficient tissue perfusion (especially involving the major organs), uncontrollable hemorrhage, multisystem organ failure primarily due to hypoxia or tissue acidosis), severe metabolism dysregulation.

In particular embodiments the treatment as herein defined prevents death of said subject.

As detailed above, the present disclosure provides a method for the treatment of a viral pathogen infection in a subject in need of such treatment, said method comprising the step of administering to said subject a therapeutically effective amount of at least one isolated peptide which specifically binds to the crystallographic homodimer interface of CD28 with a binding affinity characterized by a $K_D$ of from about 0.1 to 30 micromolar or functional derivative of said peptide having the same binding affinity.

In all aspects and embodiments, the peptide of the present disclosure also termed "a peptide as defined herein" or "a short peptide as defined herein" is to be taken to mean an isolated peptide of from about 6 to about 10 amino acid residues, that specifically binds to the crystallographic homodimer interface of human CD28 (defined by SEQ ID NO. 1), wherein the binding affinity is characterized by $K_D$ lower than about 30 micromolar, more specifically $K_D$ of from about 0.1 to 30 micromolar.

The binding affinity to the crystallographic homodimer interface may be determined by any method known in the art, for example by surface plasmon resonance spectrometry as described in [9]. The terms "crystallographic homodimer interface" and "homodimer interface" may be used herein interchangeably.

The terms "a peptide as defined herein" or "a short peptide as defined herein" are used herein interchangeably with "the present peptide(s)" or "the present isolated peptide(s)". The terms "a peptide as defined herein" or "a short peptide as defined herein" or "the present peptide" also encompass functional fragments and derivatives of the peptides, as well as pharmaceutically acceptable salts and esters thereof.

The term "amino acid" as used herein, refers to naturally occurring and synthetic amino acid residues, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. The term amino acid also encompasses D-amino acids, which are mirror images of L-amino acids, where the chirality at carbon alpha has been inverted.

The terms "amino acid sequence" or "peptide sequence" also relate to the order in which amino acid residues, connected by peptide bonds, lie in the chain in peptides and proteins. The sequence is generally reported from the N-terminal end containing free amino group to the C-terminal end containing free carboxyl group.

The term "peptide" refers to a molecular chain of amino acid residues, which, if required, can be modified at each one of its amino acid residues, for example by manosylation, glycosylation, amidation (for example C-terminal amides), carboxylation or phosphorylation. The peptide may be obtained synthetically, through genetic engineering methods, expression in a host cell, or through any other suitable means. Methods for producing peptides are well known in the art.

The term "isolated" refers to molecules, such as amino acid sequences or peptides that are removed from their natural environment, isolated or separated.

The term "isolated peptide" refers to an isolated peptide, i.e. a peptide of definite length or definite number of consecutive amino acid residues, which is not part of a longer amino acid sequence.

The terms "salts" as used herein refers to a pharmaceutically acceptable salt of a present peptide or functional derivative thereof, e.g., non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the active compounds used herein with a suitable organic or inorganic acid.

The term "ester" as used herein refers to a pharmaceutically acceptable ester, e.g. esters which retain, upon hydrolysis of the ester bond, the biological effectiveness and properties of the carboxylic acid or alcohol and are not biologically or otherwise undesirable. Generally, ester formation can be accomplished via conventional synthetic techniques.

The peptides as defined herein are generally derived from regions in the amino acid sequence of human CD28 (SEQ ID NO. 1) that harbor at least one amino acid residue of the residues forming homodimeric contacts [9, 10]. The residues forming homodimer contacts are (position in sequence SEQ ID NO. 1 is in brackets) Pro (9), Met (10), Leu (41), Val (86), Thr (89), Ile (91), Asn (111), Gly (112), Ile (114) and His (116) of the amino acid sequence of human CD28 (SEQ ID NO. 1), and define the crystallographic homodimer interface of human CD28. Regions in the human CD28 amino acid sequence from which peptides used in the present invention are derived are, for example, amino acids 10-15 and 116-121 of SEQ ID NO. 1, for example, p2TA core sequence (SEQ ID NO. 2) and p1TA core sequence (SEQ ID NO. 3), but also disclosed are peptides not specifically derived from these regions, but which comprise one or more amino acid residues of those amino acid residues which form homodimeric contacts, for example, p3TA core sequence (SEQ ID NO. 4), p4TA core sequence (SEQ ID NO. 5) or p5TA core sequence (SEQ ID NO. 6).

As detailed above, functional derivatives of the isolated peptides as defined herein are also encompassed by the present disclosure. The term "functional derivative" is meant to include functional peptide fragments and variants which differ from the isolated peptide as defined herein in one or more amino acids in the overall sequence, namely, which have deletions, insertions, substitutions (e.g. replacement of at least one amino acid by another amino acid by conservative substitution), inversions or additions. This term also encompasses the replacement of at least one amino acid residue in the overall sequence by its respective D amino acid residue. Further, this term also encompasses dimers or multimers of the present peptides. It is appreciated that these peptide fragments or derivatives do not significantly affect the biological activity of the original peptide. The terms "functional" or "without significantly affecting the biological characteristics of the modified peptide as compared to the unmodified peptide" is to be taken to mean that the modified peptide (derivative) retains a qualitative biological activity similar to that of the unmodified peptide.

The term "biological activity characteristics" when referring to the isolated peptides disclosed and used herein encompasses peptides that inhibit an inflammatory response as determined by at least one of the inflammatory cytokines IL2, interferon-γ (IFN-γ) and tumor necrosis factor-α (TNF-α) and/or by reduction in the level of cyclooxygenase 2

(cox-2), and any other suitable parameters as herein described and as known in the art.

Specific functional derivatives of the peptides as defined herein, can be any of the following:

(a) a peptide which is at least 80% homologous to a peptide as defined herein;

(b) a peptide as defined herein extended by 1-3 consecutive amino acid residues present in corresponding adjacent positions of the amino acid sequence of SEQ ID NO. 1;

(c) a peptide as defined herein, or as defined in (a) or (b), that is extended at the N terminus and/or the C terminus:

(i) by a lauryl cysteine at the N terminus and a cysteine at the C terminus; or (ii) by an organic moiety that is not a naturally occurring or synthetic amino acid residue; or (iii) by identical hydrophobic amino acid residue(s) which may be naturally occurring or synthetic amino acid residues;

(iv) by a palmitoyl-lysine tail, wherein said tail is at the N terminus; or (d) a dimer or multimer of a peptide as defined herein or the resulting peptide of any of (a), (b) or (c);

wherein the resultant peptide of any of (a), (b), (c) or (d) maintains the ability to specifically bind to the said human CD28 homodimer interface at a binding affinity characterized by $K_D$ of lower than 30 micromolar, more specifically $K_D$ of from about 0.1 to about 30 micromolar, and of achieving a therapeutic effect in the treatment of a viral pathogen infection.

By the term "homologous" as used herein it is refers to sequence similarity between two peptides. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

Specific derivatives of the peptides used in the methods, compositions, combinations and/or or kits of the present disclosure are those extended at the N-terminus and/or C-terminus thereof with D-alanine.

In some embodiments the at least one isolated peptide is any one of a peptide consisting of the amino acid sequence SPMLVAYD as denoted by SEQ ID NO. 2, also termed herein p2TA core sequence; a peptide consisting of the amino acid sequence HVKGKHLCP as denoted by SEQ ID NO. 3, also termed herein p1TA core sequence, a peptide consisting of the amino acid sequence HKGLDSAV as denoted by SEQ ID NO. 4, also termed herein p3TA core sequence, a peptide consisting of the amino acid sequence YVNQTDIY as denoted by SEQ ID NO. 5, also termed herein p4TA core sequence; or a peptide consisting of the amino acid sequence SNGTIIHVK as denoted by SEQ ID NO. 6, also termed herein p5TA core sequence, and functional derivatives thereof having the same binding affinity to the crystallographic homodimer interface of CD28, or pharmaceutically acceptable salts and esters thereof.

In various embodiments of the aspects of the present disclosure, the peptide used in the disclosed methods, compositions, combinations and/or kits is any one of the peptides having the core sequences as described herein above having D-Alanine at both termini, specifically (DA1a)-SPMLVAYD-(DA1a) as denoted by SEQ ID NO. 7, also termed herein (D-A)-p2TA-(D-A), (DA1a)-HVKGKHLCP-(DA1a), as denoted by SEQ ID NO. 8, also termed herein (D-A)-p1TA-(D-A), (DA1a)-HKGLDSAV-(DA1a), as denoted by SEQ ID NO. 9, also termed herein (D-A)-p3TA-(D-A), (DA1a)-YVNQTDIY-(DA1a), as denoted by SEQ ID NO. 10, also termed herein (D-A)-p4TA-(D-A) or (DA1a)-SNGTIIHVK-(DA1a), as denoted by SEQ ID NO. 11, also termed herein (D-A)-p5TA-(D-A).

Table 1 below presents the amino acid sequence of the crystallographic homodimer interface of human CD28 and specific peptides disclosed herein and their amino acid sequences.

TABLE 1

| SEQ ID NO. | Sequence | Type | Name |
|---|---|---|---|
| 1 | Asn Lys Ile Leu Val Lys Gln Ser Pro Met Leu Val Ala Tyr Asp Asn Ala Val Asn Leu Ser Cys Lys Tyr Ser Tyr Asn Leu Phe Ser Arg Glu Phe Arg Ala Ser Leu His Lys Gly Leu Asp Ser Ala Val Glu Val Cys Val Val Tyr Gly Asn Tyr Ser Gln Gln Leu Gln Val Tyr Ser Lys Thr Gly Phe Asn Cys Asp Gly Lys Leu Gly Asn Glu Ser Val Thr Phe Tyr Leu Gln Asn Leu Tyr Val Asn Gln Thr Asp Ile Tyr Phe Cys Lys Ile Glu Val Met Tyr Pro Pro Pro Tyr Leu Asp Asn Glu Lys Ser Asn Gly Thr Ile Ile His Val Lys Gly Lys His Leu Cys Pro Ser Pro Leu Phe Pro Gly Pro Ser Lys Pro Phe Trp Val Leu Val Val Val Gly Gly Val Leu Ala Cys Tyr Ser Leu Leu Val Thr Val Ala Phe Ile Ile Phe Trp Val Arg Ser Lys Arg Ser Arg Leu Leu His Ser Asp Tyr Met Asn Met Thr Pro Arg Arg Pro Gly Pro Thr Arg Lys His Tyr Gln Pro Tyr Ala Pro Pro Arg Asp Phe Ala Ala Tyr Arg Ser | Protein (Homo sapiens) | The crystallographic homodimer interface of human CD28 |
| 2 | SPMLVAYD | Protein (artificial) | p2TA core sequence |

TABLE 1-continued

| SEQ ID NO. | Sequence | Type | Name |
|---|---|---|---|
| 3 | HVKGKHLCP | Protein (artificial) | p1TA core sequence |
| 4 | HKGLDSAV | Protein (artificial) | p3TA core sequence |
| 5 | YVNQTDIY | Protein (artificial) | p4TA core sequence |
| 6 | SNGTIIHVK | Protein (artificial) | p5TA core sequence |
| 7 | (DAla)-SPMLVAYD-(DAla) | Protein (artificial) | (D-A)-p2TA-(D-A) |
| 8 | (DAla)-HVKGKHLCP-(DAla) | Protein (artificial) | (D-A)-p1TA-(D-A) |
| 9 | (DAla)-HKGLDSAV-(DAla) | Protein (artificial) | (D-A)-p3TA-(D-A) |
| 10 | (DAla)-YVNQTDIY-(DAla) | Protein (artificial) | (D-A)-p4TA-(D-A) |
| 11 | (DAla)-SNGTIIHVK-(DAla) | Protein (artificial) | (D-A)-p5TA-(D-A) |

In specific embodiments of all aspects of the present disclosure, the peptide used in the disclosed methods, compositions, combinations and/or kits is the peptide designated p2TA core sequence, having the amino acid sequence SPMLVAYD as denoted by SEQ ID NO. 2 or any functional fragments, derivatives, salts and esters thereof. A specific derivative is the peptide p2TA extended at both its N-terminus and C-terminus with D-alanine, designated herein (D-A)-p2TA-(D-A), having the amino acid sequence (D-A)-SPMLVAYD-(D-A) as denoted by SEQ ID NO. 7. The name p2TA (as well as all other arbitrary peptide names) can sometimes be used herein to designate both the core sequence (SEQ ID NO. 2) or its D-Ala abutted derivative (SEQ ID NO. 7). The peptide p2TA is also known as AB103, and its INN is Reltecimod, which is the sodium salt of (D-A)-p2TA-(D-A) (SEQ ID NO. 7). This peptide (i.e. SEQ ID NO. 7) is exemplified in the Examples below.

Therefore in some embodiments the at least one isolated peptide has the amino acid sequence SPMLVAYD as denoted by SEQ ID NO. 2, also termed herein p2TA, or the amino acid sequence (D-Ala)-SPMLVAYD-(D-Ala) denoted by SEQ ID NO. 7, also termed herein (D-Ala)-p2TA-(D-Ala).

In other specific embodiments of all aspects of the present disclosure, the peptide used by the method of the invention is designated p1TA core sequence and has the amino acid sequence HVKGKHLCP as denoted by SEQ ID NO. 3 or any functional fragments, derivatives, salts and esters thereof.

Other specific peptides are a peptide consisting of the amino acid sequence as denoted by SEQ ID NO. 4, designated p3TA, a peptide consisting of the amino acid sequence as denoted by SEQ ID NO. 5, designated p4TA, and a peptide consisting of the amino acid sequence as denoted by SEQ ID NO. 6, designated p5TA. These peptides exhibit biological activity similar to that of p2TA [9].

The D-Ala derivatives (peptide core sequence extended at both its C and N termini with D-alanine residue) and palmitoyl-lysine derivatives (peptide core sequence extended at its N terminus with palmitoyl-lysine tail) are also encompassed hereby.

As detailed above the present disclosure provides a method for the treatment of a viral pathogen infection in a subject in need of such treatment. In the Examples below a beneficial effect was shown by the peptide as defined herein in the treatment of viral infections caused by avian Influenza type A virus subtype H5N1 and swine Influenza type A virus subtype H1N1.

Generally, the term "viruses" is used in its broadest sense to include flaviviruses, haemorrhagic fever viruses such as West Nile virus and ZIKA virus, coronaviruses, adenoviruses, papovaviruses, herpesviruses, such as herpes simplex, varicella-zoster or Epstein-Barr, CMV, pox viruses such as smallpox or vaccinia; hepatitis A, hepatitis B, hepatitis C, rhinoviruses, rubella virus, arboviruses, Orthomyxoviridae viruses such as influenza viruses A and B; measles virus, mumps virus, Filoviridae members such as Ebola virus and Marburg virus, virus as well as others, as described in more detail below.

In some embodiments of aspects of the present disclosure, the viral pathogen is a virus of any one of the Orthomyxoviridae, Filoviridae, Flaviviridae, Coronaviridae or Poxviridae families, and subfamilies thereof.

Viral pathogen infection may be diagnosed by a physician.

The Orthomyxoviridae family as known in the art is a family of RNA viruses that includes Influenza virus A, B, C and D, Isavirus, Thogotovirus and Quaranjavirus. The first three genera contain viruses that cause influenza in vertebrates, including birds, humans, and other mammals.

In specific embodiments of aspects of the present disclosure, the said viral pathogen is a virus of the Orthomyxoviridae, family, such as, but not limited to, Influenza virus type A, Influenza virus type B, Influenza virus type C (also referred to as Influenza virus A, B or C) or any subtype or reassortants thereof.

Methods, compositions, combinations and kits according to the present disclosure provided for the treatment of viral infection by a large number of viruses. These include, but are not limited to, the following specific viruses, described in detail.

Influenza A and B virus particles contain a genome of negative sense, single-strand RNA divided into 8 linear segments. Co-infection of a single host with two different influenza viruses may result in the generation of reassortant progeny viruses having a new combination of genome segments, derived from each of the parental viruses. Type A influenza viruses are divided into subtypes based on two proteins on the surface of the virus, hemagglutinin (HA) and neuraminidase (NA). There are 15 different HA subtypes and 9 different NA subtypes. Subtypes of influenza A virus are named according to their HA and NA surface proteins. For example, an "H7N2 virus" designates influenza A subtype that has an HA 7 protein and an NA 2 protein, etc. All known subtypes of A viruses can be found in birds. Symptoms of human infection with avian viruses have ranged from typical flu-like symptoms (fever, cough, sore throat and muscle aches) to eye infections, pneumonia, severe respiratory diseases (such as acute respiratory distress), and other severe and life-threatening complications. The symptoms of bird flu may depend on which virus caused the infection. Each of avian influenza A viruses H5, H7, and H9 theoretically can be partnered with any one of nine neuraminidase surface proteins; thus, there are potentially nine different forms of each subtype (e.g., H5N1 to H5N9). H5 infections have been documented in humans, sometimes causing severe illness and death. H7 infection in humans is rare, but can occur among persons who have direct contact with infected birds. It is believed that most cases of bird flu infection in humans have resulted from contact with infected poultry or contaminated surfaces. The risk from bird flu is generally low to most people because the viruses occur mainly among birds and do not usually infect humans. However, the current outbreak of avian influenza A (H5N1) among poultry in Asia and Europe is an example of a bird flu outbreak that has caused human infections and deaths.

In particular embodiments of all aspects of the present disclosure, the viral pathogen is avian Influenza virus type A virus, or any subtype and reassortant thereof. In other particular embodiments of all aspects of the present disclosure, the viral pathogen is avian Influenza type A virus has haemagglutinin component of subtype H5, H7 or H9.

Reassortment and new Influenza subtype formation Influenza A viruses are found in many different animals, including ducks, chickens, pigs, whales, horses, and seals.

However, certain subtypes of influenza A virus are specific to certain species, except for birds which are hosts to all subtypes of influenza A. Influenza A viruses normally seen in one species can cross over and cause illness in another species. For example, H5N1 avian influenza was responsible for a recent outbreak of bird flu in the human population, while H7N7, H9N2 and H7N2 subtypes have also been associated with transmission over the species barrier and resultant infection in humans. H1N1 is associated with the 2009 swine influenza virus pandemic.

Therefore in some particular embodiments of all aspects of the present disclosure, the viral pathogen is swine Influenza type A virus subtype H1N1. In further specific embodiments of all aspects of the present disclosure, the viral pathogen is avian Influenza type A virus subtype H5N1.

Avian influenza viruses may be transmitted to humans in two main ways; (a) directly from infected birds or from material contaminated with avian influenza virus, (b) through an intermediate host, such as a pig.

Influenza viruses have eight separate gene segments. The segmented genome allows viruses from different species to mix and create a new influenza A virus if viruses from two different species infect the same person or animal. For example, if a pig were infected with a human influenza virus and an avian influenza virus at the same time, the viruses could reassort and produce a new virus that had most of the genes from the human virus, but a hemagglutinin and/or neuraminidase from the avian virus. The resulting new virus might then be able to infect humans and spread from person to person, but it would have surface proteins (hemagglutinin and/or neuraminidase) not previously seen in influenza viruses that infect humans. This type of major change in the influenza A viruses is known as antigenic shift. Antigenic shift results when a new influenza A subtype to which most people have little or no immune protection infects humans. If this new virus causes illness in people and can be transmitted easily from person to person, an influenza pandemic can occur.

It also is possible that the process of reassortment could occur in a human who was infected with avian influenza and a human strain of influenza. Virus reassortment could create a new virus with haemagglutinin from the avian virus and other genes from the human virus. Theoretically, influenza A viruses with a haemagglutinin against which humans has little or no immunity that have reassorted with a human influenza virus are more likely to result in sustained human-to-human transmission and pandemic influenza.

As mentioned, infection with type A Influenza virus in humans is generally caused by subtypes comprising H1, H2 and H3 haemagglutinin subtypes which are combined with one of either the N1 or N2 neuraminidase subtypes. Type A influenza virus which is derived from, and is primarily infectious to avian, but which has crossed the species barrier to cause infection in humans has been observed for type A influenza virus with haemagglutinin subtypes H5, H7 and H9. These strains, such as H5N1, H7N2, H7N3 and H9N2 comprise avian H and N subtypes. The swine influenza A subtype H1N1 is a reassortant of 5 strains of avian, swine and human origin. Reassortment of viruses in a host co-infected with both an avian type A influenza virus and a human type A influenza virus may result in a virus wherein an H or N component from a human adapted type A influenza virus reassorts with an avian influenza virus.

Thus, the methods, peptides, uses, combinations compositions and kits of the present disclosure can be effective against avian influenza variants which resulted from both antigenic drift and antigenic shift, and have efficacy against new strains of type A influenza virus irrespective of what antigenic shift mutations to the viral genome occur.

Therefore, all aspects and embodiments of the present disclosure, peptides, methods, uses, combinations, compositions and kits, extend to treatment of an infection by influenza subtype which has resulted from natural reassortment of human influenza virus with avian influenza virus to form a new influenza virus variant, and to treatment of infection by an influenza subtype which has resulted from natural reassortment of human, swine and avian influenza viruses to form a new influenza virus variant.

In some embodiments, the influenza virus which resulted from reassortment may contain an avian haemagglutinin subtype and a human adapted neuraminidase subtype; or alternatively a human adapted haemagglutinin subtype and an avian neuraminidase subtype. In one specific embodiment, the virus subtype may be H5N1 wherein the neuraminidase subtype is derived from an avian type A influenza virus and the haemagglutinin component is derived from a human adapted type A influenza virus.

In some embodiments, a specific viral pathogen is avian Influenza virus type A, which may comprise haemagglutinin component of subtype H1, H5, H7 or H9, for example, the H5N1 subtype. According to other specific embodiments, the methods, peptides, compositions and/or combinations of the present disclosure may be used for treating infection with Influenza A of any one of the H5N1, H1N1, H2N2 and H3N3 subtypes, specifically Influenza A subtype H5N1 and/or subtype H1N1. As shown in the following Examples, treatment leads to controlling, attenuating and/or inhibiting cytokine storm caused by the viral infection, and side effects thereof.

In further aspects and embodiments of the present disclosure, the viral pathogen can be a virus belonging to the filoviridea family, also referred to herein as "Filoviruses". These are generally single-stranded negative sense RNA viruses that typically infect primates. Filoviruses are able to multiply in virtually all cell types. The filovirus genome comprises seven genes that encode 4 virion structural proteins (VP30, VP35, nucleoprotein, and a polymerase protein (L-pol)) and 3 membrane-associated proteins (VP40, glycoprotein (GP), and VP24). Filoviruses cause hemorrhagic fevers with high levels of fatality. They are classified in two genera within the family Filoviridae: Ebola virus (EBOV) and Marburg virus (MARV), both being highly pathogenic in humans and nonhuman primates, with case fatality levels of up to 90%. Ebola virus species Reston (REBOV) is pathogenic in monkeys but does not cause disease in humans or great apes. Fatal outcome in filoviral infection is associated with an early reduction in the number of circulating T cells, failure to develop specific humoral immunity, and the release of pro-inflammatory cytokines. More specifically, these viruses cause sporadic epidemics of human disease characterized by systemic hemorrhage, multi-organ failure and death in most instances. The onset of illness is abrupt, and initial symptoms resemble those of an influenza-like syndrome. Fever, headache, general malaise, myalgia, joint pain, and sore throat are commonly followed by diarrhea and abdominal pain. A transient morbilliform skin rash, which subsequently desquamates, often appears at the end of the first week of illness. Other physical findings include pharyngitis, which is frequently exudative, and occasionally conjunctivitis, jaundice, and edema. After the third day of illness, hemorrhagic manifestations are common and include petechiae as well as frank bleeding, which can arise from any part of the gastrointestinal tract and from multiple other sites. As the disease progresses, patients develop severe multifocal necroses and a syndrome resembling septic shock. In addition, activation of the fibrinolytic system coupled with the consumption of coagulation factors results in a depletion of clotting factors and degradation of platelet membrane glycoproteins.

In still further aspects and embodiments of the present disclosure, as briefly described above, the viral pathogen can be a virus belonging to the Flaviviridea family, also referred to herein as "Flaviviruses", specifically West Nile virus (WNV), Dengue virus (DENV), Yellow Fever virus (YFV) or the Zika virus (ZIKV), which are usually mosquito-borne. Several genotypes are known for each of these viruses. WNV causes West Nile Fever, which can be manifested by fever, headache, vomiting, or a rash. Encephalitis or meningitis are rather rare. Recovery may take weeks to months. DNV is the cause for Dengue fever, with symptoms typically beginning three to fourteen days after infection, which may include a high fever, headache, vomiting, muscle and joint pains, and a characteristic skin rash. Recovery generally takes two to seven days. In a small proportion of cases, the disease develops into the life-threatening dengue hemorrhagic fever, resulting in bleeding, low levels of blood platelets and blood plasma leakage, or into dengue shock syndrome, where dangerously low blood pressure occurs. YFV causes Yellow Fever, viral disease of typically short duration. In most cases, symptoms include fever, chills, loss of appetite, nausea, muscle pains particularly in the back, and headaches. Symptoms typically improve within five days. In about 15% of people, within a day of improving the fever comes back, abdominal pain occurs, and liver damage begins causing yellow skin. If this occurs, the risk of bleeding and kidney problems is also increased. ZKV causes a self-limiting, dengue fever (DF)-like disease with an incubation time of up to 10 days. Signs and symptoms consist of rather low-grade fever, myalgia and a maculopapular rash, accompanied by arthralgia and headache, and less often edema, sore throat, and vomiting. There have been ZIKV outbreaks in 2007 and in 2013, and an epidemic after its introduction to Brazil in 2016, all attributed to the Asian genotype of ZIKV. In contrast to DF, acute Zika fever (ZF) is less severe. A recent study has shown that polyfunctional T cell activation (Th1, Th2, Th9 and Th17 response) was seen during the acute phase of Zika DF, characterized by increase in respective cytokines levels (IL-2, IL-3, IL-13, IL-9 and IL-17), followed by a decrease in the reconvalescent phase [11]. ZIKV infections are associated with Gillain-Barrè syndrome. In pregnancy the disease spreads from mother to fetus in the womb, and can cause multiple problems in the baby, most notably microcephaly, as well as eye abnormalities and hydrops fetalis.

Thus, in some embodiments the viral pathogen as herein defined is a virus of the Filoviridae family comprising Marburg virus (MARV) and Ebola virus (EBOV), or said viral pathogen is a virus of the Flaviviridae family comprising Zika virus (ZIKV), West Nile virus (WNV), Dengue virus (DENV) and Yellow Fever virus (YFV).

In particular embodiments the symptom or damage associated with the viral infection is any one of fever, for example Zika fever, West Nile fever, Dengue fever or Yellow fever, where fever is usually accompanied by at least one of headaches, vomiting, skin rash, muscle and joint pains, and a characteristic skin rash, and other effects, e.g. as described above.

In other particular embodiments of aspects of the present disclosure, the viral pathogen is a Coronaviridae family member, more particularly the Severe Acute Respiratory Syndrome (SARS) virus (SARS-CoV), causing a viral respiratory disease of zoonotic origin (outbreaks in 2002-2003, in southern China caused an eventual 8,098 cases, resulting in 774 deaths reported in 37 countries). Initial symptoms are flu-like and may include fever, muscle pain, lethargy symptoms, cough, sore throat, and other nonspecific symptoms. The only symptom common to all patients appears to be a fever above 38° C. (100° F.). SARS may eventually lead to shortness of breath and/or pneumonia; either direct viral pneumonia or secondary bacterial pneumonia. The average incubation period for SARS is 4-6 days, although rarely it could be as short as 1 day or as long as 14 days. There have been no outbreaks since 2004. No vaccine is available.

In a further, third aspect, the present disclosure provides a method for preventing worsening of, arresting and/or ameliorating at least one symptom of a viral infection in a subject in need thereof, or preventing damage to said subject or an organ or tissue of said subject, emanating from or associated with said viral infection, and preventing death, said method comprising the step of administering to said subject a therapeutically effective amount of at least one isolated peptide as defined herein or functional derivative thereof, or a composition comprising said at least one isolated peptide or functional derivative thereof, said method further optionally comprising a step of administering to said subject at least one additional antiviral therapeutic agent.

The said symptom of the viral infection or said damage can be at least one of fever (temperature of >38° C.), acute respiratory distress syndrome (ARDS), multiple organ dysfunction syndrome (MODS), systemic inflammatory response syndrome (SIRS), Zika fever (dengue-like fever) hypotension, tachycardia, dyspnea, ischemia, or insufficient tissue perfusion (especially involving the major organs), uncontrollable hemorrhage, multisystem organ failure (caused primarily by hypoxia, tissue acidosis), severe metabolism dysregulation. Treatment in accordance with this aspect of the present disclosure can prevent death of the treated subject.

As shown in the Examples below, the CD28 dimer interface mimetic peptide p2TA protects mice partially from lethal H1N1 or H5N1 influenza infection and synergizes in a pronounced manner with the antiviral agent, Oseltamivir. The concept of using a host-oriented therapeutic against influenza avoids the rapid emergence of pathogen resistance that has characterized agents that target viral gene products, such as neuraminidase inhibitors. For example, Oseltamivir resistance among pandemic flu strains is increasingly becoming a major problem. The experiments presented below suggest that the host-oriented therapeutic peptide p2TA may be used effectively in synergy with low concentrations of an antiviral drug. p2TA synergizes potently with sub-therapeutic concentrations of, for example, Oseltamivir, to achieve full protection at doses of neuraminidase inhibitor that are low and hence less prone to eliciting viral resistance. This confers an important advantage over the use of antiviral agents alone.

In addition, as shown in Examples 2, p2TA itself, without any additional antiviral agent, was able to provide at least partial protection from the lethal effect of H1N1 and H5N1 infections. The peptide promoted recovery of the mice from weight loss, improved their lung function, and caused a significant reduction in the inflammatory cytokine response in the lungs of the infected animals.

Therefore and as detailed above in particular embodiments the method for the treatment of a viral pathogen infection as herein defined comprises administering to said subject a therapeutically effective amount of at least one isolated peptide as herein defined and optionally administering to said subject at least one additional antiviral therapeutic agent.

Thus, in specific embodiments the method of the present disclosure further comprises the step of administering to said subject a therapeutically effective amount of at least one additional antiviral therapeutic agent.

The term "additional antiviral therapeutic agent" encompasses any antiviral therapeutic agent known in the art.

In particular embodiments of all aspects of the present disclosure, the additional antiviral therapeutic agent is other than an antibody directed against said viral pathogen.

In other words the present disclosure further provides a method for the treatment of a viral pathogen infection in a subject in need of such treatment, said method comprising the step of administering to said subject a therapeutically effective amount of at least one isolated peptide which specifically binds to the crystallographic homodimer interface of CD28 with a binding affinity characterized by a $K_D$ of from about 0.1 to 30 micromolar or functional derivative of said peptide having the same binding affinity, or a composition comprising said at least one isolated peptide or functional derivative thereof, said method further comprising a step of administering to said subject at least one additional antiviral therapeutic agent, wherein said additional antiviral therapeutic agent is other than an antibody directed against said viral pathogen.

According to aspects and embodiments of the present disclosure, where an additional antiviral therapeutic agent is used, such agent may be, for example but not limited to, a viral neuraminidase inhibitor (for example Oseltamivir or Zanamivir), a viral polymerase inhibitor (for example Ribavirin) or M2 ion-channel blocker (for example amantadine or rimantadine).

Any known approved viral neuraminidase inhibitor may be used together with the present peptides in the methods, compositions, combinations and kits of the present disclosure. The term "neuraminidase inhibitor" as known in the art relates to a class of anti-viral agents that block the neuraminidase enzyme. These agents are commonly used as antiviral drugs since they block the function of viral neuraminidases of the influenza virus, by preventing its reproduction by budding from the host cell. Examples of neuraminidase inhibitors include but are not limited to Tamiflu® (Oseltamivir phosphate), Gilead/Roche (oral neuraminidase inhibitor), Relenza® (Zanamivir), Biota/GlaxoSmithKline (inhaled neuraminidase inhibitor). It should be noted that the use of phase II inhibitors such as: T-705 Toyama Chemical Co. (oral polymerase inhibitor), Peramivir®, BioCryst (IV/IM neuraminidase inhibitor), or phase I inhibitors such as CS-8958, Biota/Daiichi Sankyo (inhaled neuraminidase inhibitor) is also encompassed by the scope of the present disclosure.

Viral DNA and RNA polymerases are enzymes responsible for copying the genetic materials of viruses and are therefore central targets for development of new anti-viral agents. Therefore the term "viral polymerase inhibitor" as known in the art and as used herein refers to any agent that attenuates, inhibits or interferes with the activity of viral DNA and RNA polymerases. Few non limiting examples for such inhibitors are favipravir and sofosbuvir.

The term "M2 ion-channel blocker" (also called "M2 proton channel blocker") as known in the art and as used herein refers to agents that function by blocking the ion channel activity of a viral protein, which is mainly required during virus entry into the host cells in the early phase of the replication life cycle, for example but not limited to Amantadine and Rimantadine.

Therefore in some embodiments the at least one additional antiviral therapeutic agent is any one of a viral neuraminidase inhibitor, a viral polymerase inhibitor and an M2 ion-channel blocker.

In particular further embodiments the at least one additional antiviral therapeutic agent is Oseltamivir or Zanamivir.

As known in the art, Oseltamivir (also known as "Tamiflu") is an antiviral neuraminidase inhibitor used to treat and prevent influenza A and influenza B viral infections and is generally recommended for people who have complications or are at high risk of complications within 48 hours of the first symptoms of infection.

As known in the art, Zanamivir is a neuraminidase inhibitor used to treat and prevent influenza caused by influenza A and B viruses in otherwise-healthy individuals.

The therapeutic potential of the peptide (D-Ala)-p2TA-(D-Ala) in combination with Oseltamivir when the latter was used at suboptimal dose was demonstrated by the Inventors in Example 1 below. Therefore in some particular embodiments the at least one additional antiviral therapeutic agent is administered to said subject at either a suboptimal dose or at a therapeutic dose.

The term "suboptimal dose" as used herein refers to a dose lower than the dose known in the art for treatment of the viral infection. In some specific embodiments suboptimal dose may be lower by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or about 99% than the dose known in the art for treatment of the viral infection.

In the above and other embodiments the peptides as described herein and the additional antiviral agent are administered in a therapeutically effective amount (also referred herein "therapeutic dose"). A therapeutically "effective amount" or "therapeutic dose" for purposes herein is that determined by such considerations as are known in the art. The amount must be sufficient to inhibit, prevent worsening of, arrest and/or ameliorate at least of one symptom of the said viral infection in the treated subject, and/or prevent damage to said subject or an organ or tissue of the subject emanating from or associated with said viral infection by the infecting virus, which may lead to cytokine storm. The said at least one symptom of the said viral infection or damage to said subject or an organ or tissue of the subject, emanating from or associated with said viral infection is at least one of fever (temperature of >38° C.), acute respiratory distress syndrome (ARDS), multiple organ dysfunction syndrome (MODS), systemic inflammatory response syndrome (SIRS), hypotension, tachycardia, dyspnea, ischemia, insufficient tissue perfusion (especially involving the major organs), uncontrollable hemorrhage, multisystem organ failure primarily due to hypoxia or tissue acidosis), severe metabolism dysregulation.

The terms "treat", or forms thereof, and also the terms "prevent worsening", "arrest", and "ameliorate" and forms thereof mean to at least partially cure the patient's disease or condition.

By the term "achieving a therapeutic effect" it is meant, for example, slowing down or preventing the progression of viral infection symptoms, preventing worsening, arresting and/or ameliorating at least one of the viral infection symptoms, preventing damage to the treated subject or to an organ or tissue of said subject, emanating from or associated with said viral infection, and preventing death of the subject.

Treatment with any of the compositions, combined compositions or kits of the present disclosure may increase survival of the treated subjects by at least 10%, at least 15%, at least 20%, at least 25%, at least 30%, at least 40%, at least 50%, at least 60%, at least 70%, at least 80% or even by at least 90% or 100% as compared to the survival of untreated subjects.

It is further noted that treatment with any of the compositions, combined compositions and kits of the invention may improve any measured parameter for lung function, for example, the oxygen saturation, that may increase by at least 5%, at least 10%, at least 15%, at least 20%, at least 25%, at least 30%, at least 40%, at least 50% or even at least 80%, 90% or 100% as compared to the level prior to treatment. Similar improvement may be also shown in parameters such as body weight, and lung lobe histology.

By the term "a subject in need of such treatment" as referred to herein it is meant a subject (human, animal) diagnosed as inflicted with a viral pathogen infection by a skilled physician. The symptoms of the viral infection or damage to said subject or an organ or tissue of said subject, emanating from or associated with said viral infection are well known to a skilled physician.

Although the methods, peptides, uses, compositions, combinations and kits of the present disclosure are particularly intended for the treatment viral infection in mammals, particularly humans, other mammals, and also avian and particularly domestic birds are included. Domestic birds may be but are not limited to chicken, turkeys, geese, ducks, pheasants, quails, pigeons and ostriches. By way of non-limiting examples, mammalian subjects also include monkeys, equines, cattle, canines, felines, rodents such as mice and rats, and pigs.

Therefore in the above and other embodiments the subject is a human subject. In other particular embodiments the subject is an avian (a bird).

In a further aspect the present disclosure provides at least one isolated peptide which specifically binds to the crystallographic homodimer interface of CD28 with a binding affinity characterized by a $K_D$ of from about 0.1 to 30 micromolar or functional derivative of said peptide having the same binding affinity, or a composition comprising said at least one isolated peptide or functional derivative thereof, for use in a method for treatment of a viral pathogen infection in a subject in need of such treatment, said method further optionally comprising administering to said subject at least one additional antiviral therapeutic agent.

Also disclosed herein is a combination comprising at least one isolated peptide which specifically binds to the crystallographic homodimer interface of CD28 with a binding affinity characterized by a $K_D$ of from about 0.1 to 30 micromolar or functional derivative of said peptide having the same binding affinity and at least one additional antiviral therapeutic agent.

In embodiments of the disclosed therapeutic combination, the said additional antiviral therapeutic agent is other than an antibody directed against the viral pathogen.

The disclosed combination provides for a safe, non-interfering, synergistic or additive therapy, particularly for therapeutic treatment of a viral infection.

The at least one additional therapeutic antiviral agent in the disclosed combination can be, for example, a neuraminidase inhibitor, a viral polymerase inhibitor and/or at least one M2 ion channel blocker as the additional antiviral agent. Some such synergistic combination therapies are described in the following Examples, and are useful in treating subjects suffering from a viral pathogen infection symptoms or damages associated therewith or emanating therefrom.

In a particular embodiment the combination in accordance with the present disclosure comprises as a peptide as defined herein the p2TA peptide core sequence (SEQ ID NO. 2) or its D-Ala derivative ((D-A)-p2TA-(D-A) (SEQ ID NO. 7), and said at least one antiviral agent is a neuraminidase inhibitor, specifically oseltamivir.

By "synergic" as defined herein, with reference to any of the presently disclosed methods, peptides, uses, compositions, combinations and kits, is meant that the effect of both peptide as defined herein and additional antiviral therapeutic agent is greater than the sum of the therapeutic effects of administration of any of these compounds separately, as a sole treatment. The increase in the effect of the peptide as defined herein in combination with the additional antiviral therapeutic agent relative to the effect of the peptide as defined herein and additional antiviral therapeutic agent when administered each as a sole treatment may be measured by one skilled in the art for example by using the models described by the Inventors herein below.

By "additive effect" as used herein is meant that the effect of the peptide as defined herein in combination with the said additional antiviral therapeutic agent is substantially the sum of the therapeutic effects of administration of any of these compounds separately, as a sole treatment. It is to be appreciated that in embodiments of the present disclosure in which both a peptide as defined herein and an additional antiviral therapeutic agent are employed, particularly when the additional therapeutic antiviral agent is used in suboptimal dose, and nonetheless a therapeutic effect is achieved, the additive effect is an improvement over using optimal doses of the antiviral agent. Thus, these methods of the present disclosure provide for a therapeutic effect using low doses of the additional antiviral agent, which is generally clinically desired.

In further specific embodiments, the combination of the present disclosure is for use in the treatment of a viral pathogen infection in a subject in need of such treatment.

In other words the present disclosure further provides a combination comprising at least one isolated peptide which specifically binds to the crystallographic homodimer interface of CD28 with a binding affinity characterized by a $K_D$ of from about 0.1 to 30 micromolar or functional derivative of said peptide having the same binding affinity and at least one additional antiviral therapeutic agent for use in the treatment of a viral pathogen infection in a subject in need of such treatment.

It should be appreciated that the active compounds, namely the at least one peptide as defined herein and the at least one additional antiviral therapeutic agent, can be generally comprised in and administered in the form of a pharmaceutical composition, comprising either one or both compounds of this disclosure (peptides as defined herein or any combination thereof together with an antiviral therapeutic agent), optionally together with pharmaceutically acceptable additives, carriers, diluents and excipients.

Alternatively, each active compound is administered individually, at times in the form of a pharmaceutical composition comprising the same, optionally together with pharmaceutically acceptable additives, carriers, diluents and excipients. Thus, the active compounds used in the presently disclosed methods of treatment viral infection can be provided in the same composition or separately, for example in a kit. Whether combined in the same composition or in separate compositions, each of the active agents or compositions comprising the same can be provided in any conventional oral or injectable or otherwise administrable dosage form, such as, for example, compositions for inhalation, etc. The present compositions can also comprise additional active agents, e.g. protease inhibitors.

Thus, in a further, aspect, provided herein is a kit comprising the presently disclosed active compounds and/or compositions thereof. The kit in accordance with the present disclosure can include individually the two pharmaceutically active compounds, namely a peptide as disclosed herein and an additional antiviral agent. Each of the active compounds, namely the peptide and the additional antiviral agent, or compositions comprising the same, can be comprised in a separate unit dosage form, the kit thus containing two individual first and second unit dosage forms, respectively. The kit can include container means for containing both active compounds, the peptide and the additional antiviral agent, and/or compositions thereof, such as a divided bottle or a divided foil packet. However, the separate active compounds or compositions thereof can also be contained within a single, undivided container. The separate active compounds, namely the peptide and the additional antiviral agent, or compositions thereof, can also be comprised in a single composition, optionally further comprising a pharmaceutically acceptable additive, carrier or diluent, where the at least one peptide and additional antiviral agent are chemically and pharmacologically compatible, for example, where there is no drug-drug interaction between them.

In other words the present disclosure further provides a kit for the treatment of a viral pathogen infection and/or at least one symptom thereof in a human subject in need of such treatment, comprising:

(a) at least one isolated peptide which specifically binds to the crystallographic homodimer interface of CD28 with a binding affinity characterized by a $K_D$ of from about 0.1 to 30 micromolar, optionally comprised in a composition further comprising a pharmaceutically acceptable carrier or diluent, optionally in a first dosage unit form;

(b) an additional antiviral therapeutic agent, optionally comprised in a composition further comprising a pharmaceutically acceptable carrier or diluent, optionally in a second dosage unit form;

(c) container means for containing said first and second dosage forms jointly or separately;

(d) instructions for use; and optionally (e) means for administering said at least one isolated peptide and said at least one additional antiviral therapeutic agent to said subject.

In particular embodiments the kit of the present disclosure is wherein said additional antiviral therapeutic agent is other than an antibody directed against said viral pathogen.

Typically the disclosed kit includes directions for the administration of the separate or combined active compounds. The kit form is particularly advantageous when the separate active compounds are administered in different dosage forms (e.g., oral and injectable, for example intravenous or intraperitoneal), are administered at different dosage intervals, or when titration of the individual components of the combination is desired by the prescribing physician. The kit of the present disclosure can optionally further comprise means for administering the different active compounds, the peptides of the invention and the additional antiviral therapeutic agent, or compositions thereof.

According to one embodiment, the disclosed kit is intended for achieving a therapeutic effect in a subject suffering from an infection caused by a viral pathogen, or at least one of the symptoms thereof, as described herein.

In other words, in specific embodiments the kit of the present disclosure is for use in the treatment of a viral pathogen infection in a subject in need of such treatment.

Still further, the present disclosure provides for a method of treatment of a cytokine storm-related disorder caused by a viral pathogen comprising the step of administering to a subject in need thereof a therapeutically effective amount of a peptide as defined herein, optionally comprised in a first dosage unit and an additional antiviral agent, optionally comprised in a second unit dosage form, as comprised in the kit according to the present disclosure.

It is to be appreciated that both components of the kit, the peptide as defined herein (e.g. in the first dosage form) and the antiviral therapeutic agent (e.g. in the second dosage form) can be administered to the subject simultaneously or sequentially in any order.

As shown by the results of Example 1, a daily dose of the active ingredients in specific methods, uses, combinations, compositions or kits of the present disclosure may contain between about 0.5 μg/kg body weight to about 5.0 mg/kg, of any of the peptides of the invention. According to a specific embodiment, the effective amount may be any one of 0.5, 1, 5, 10, 20, 30, 40, 50, 60, 70, 80, 90, 100, 150, 180, 200, 250, 300, 350, 400, 450, 500, 1000, 2000, 3000, 4000 and 5000 μg/kg, per day of any of the peptides of the invention, and between about 0.1 to 250, specifically, 0.5 to 200 mg/kg per day of the additional antiviral therapeutic agent, such as about 0.5, 1, 5, 10, 15, 20, 25, 30, 40, 50, 75, 100, 150, 200 and up to 250 mg/kg per day of, for example, a neuraminidase inhibitor. In a particular embodiment, where the p2TA peptide is used, a preferred amount may be 20, 50, 180 or 500 μg/kg/day, and about 1 mg/kg of a neuraminidase inhibitor such as Oseltamivir, at a quantitative ratio that may range between about 1:0.1 to 1:1000. These effective amounts of the peptides of the invention and the antiviral therapeutic agents may be optionally comprised within a dosage unit form.

In particular embodiments the isolated peptide of the present disclosure is administered to said human subject at an amount of from about 0.05 mg to about 0.5 mg peptide/kg body weight of said subject.

Treatment of different conditions may dictate the use of different doses of each of the active ingredients, at and for different time periods, as will be evident to the skilled medical practitioner.

The said therapeutically effective amount or dosage to be administered to the subject, is dependent on severity and responsiveness of the disease state to be treated, with the course of treatment lasting from 1 to several days or weeks, or until a cure is effected or relief of the disease state and symptoms is achieved. Optimal dosing schedules can be calculated from measurements of drug accumulation in the body of the patient. Persons of ordinary skill can easily determine optimum dosages, dosing methodologies and repetition rates. In general, dosage is calculated according to body weight, and may be given once or more daily, weekly, or monthly. Persons of ordinary skill in the art can easily estimate repetition rates for dosing based on measured residence times and concentrations of the active compounds in bodily fluids or tissues.

Different combinations of different ratios at different concentrations of at least one of the peptides as herein defined, particularly, the p2TA peptide core sequence (SEQ ID NO. 2) or its D-ala derivative (D-A)-p2TA-(D-A) (SEQ ID NO. 7), and at least one antiviral therapeutic agent, such as Oseltamivir, may be used for different viral infections, or different symptoms of the viral infection. It should be appreciated that any quantitative ratio may be used, for example: 1:1000, 1:2, 1:50, 1:200, 1:350, 1:500 and any possible combination.

In particular embodiments of the method, peptide, combination, kit and uses thereof of the present disclosure the at least one isolated peptide and the at least one additional antiviral therapeutic agent are administered to said subject at different time points, at different intervals between administrations, for different treatment periods, and/or at any order of administration.

In further particular embodiments of the method, peptide, combination, kit and uses thereof of the present disclosure each one of said isolated peptide or composition comprising the same and said additional antiviral therapeutic agent is administered at one or more identical or different treatment periods of one or more weeks of once daily, once every three days, once every five days or once weekly administrations of each of said isolated peptide and said additional antiviral agent, wherein said treatment periods are consecutive or are set apart from each other by non-treatment intervals of 1 or several days or 1 or several weeks.

Additionally, the administration of the combined composition or the kit according to the invention may be periodically, for example, the periodic administration may be effected twice daily, three time daily, or at least once daily for at least about one day to about two weeks or more. The advantages of lower doses of any drug are evident to those of skill in the art. These include, inter alia, a lower risk of side effects, a lower risk of the patients becoming desensitized to the treatment, and lower cost.

Treatment using the methods, peptides, uses, combinations, compositions and kits of the present disclosure can be administered for at least 1, 2, 3, 4 or 5, days, or longer, as determined by the attending medical personnel.

In various embodiments of the method, peptide, combination, kit and uses thereof of the present disclosure the at least one isolated peptide and the at least one additional antiviral therapeutic agent are administered to said subject simultaneously or consecutively, where the peptide of the present disclosure may be administered before or after administration of said additional antiviral therapeutic agent.

In particular embodiments the at least one isolated peptide and the at least one additional antiviral therapeutic agent are administered to said subject simultaneously.

In particular embodiments of the method, peptide, combination, kit and uses thereof of the present disclosure the peptide of the present disclosure is administered by a single administration of a single dose thereof.

In various embodiments of the method, peptide, combination, kit and uses thereof of the present disclosure each one of said isolated peptide or composition comprising the same and said additional antiviral agent is administered to said subject immediately following, or within from about 30 minutes up to about 10 days following exposure to the virus, before or after manifestation of clinical symptoms/damage, specifically symptoms/damage as described herein, optionally by a single administration of a single dose thereof.

Determining the time at which the subject was exposed to the virus (or in other words when exposure to the virus has occurred) is within the capacity of a skilled physician.

In further embodiments of the method, peptide, combination, kit and uses thereof of the present disclosure the interval between administration of said at least one isolated peptide and said at least one additional antiviral therapeutic agent is between about 5 minutes to about 5 hours.

The peptides as defined herein can be synthesized using standard methods known in the art. Direct synthesis of the peptides of the invention may be accomplished using solid-phase peptide synthesis, solution-phase synthesis or other conventional means. For example, in solid-phase synthesis, a suitably protected amino acid residue is attached through its carboxyl group to an insoluble polymeric support, such as a cross-linked polystyrene or polyamide resin. In our context, a protected amino acid refers to the presence of protecting groups on both the amino group of the amino acid, as well as on any side chain functional groups. The benefit of side chain protecting groups are that they are generally stable to the solvents, reagents, and reaction conditions used throughout the synthesis and are removable without affecting the final peptide product. Typically, stepwise synthesis of the polypeptide is carried out by the removal of the N-protecting group from the initial carboxy terminal and coupling it to the next amino acid in the sequence of the polypeptide. The carboxyl group of the incoming amino acid can be activated to react with the N-terminus of the bound amino acid by formation into a reactive group such as formation into a carbodiimide, a symmetric acid anhydride, or an active ester group such as hydroxybenzotriazole or pentafluorophenyl esters. The solid-phase peptide synthesis methods include both the BOC and FMOC methods, which utilizes tert-butyloxycarbonyl, and 9-fluorenylmethloxycarbonyl as the α-amino protecting groups, respectively, both well-known by those of skill in the art (Sambrook et al., Molecular Cloning: A Laboratory Manual, 2nd edition, Cold Spring Harbor Press, Cold Spring Harbor, N.Y.; Ausubel et al., Current Protocols in Molecular Biology, John Wiley and Sons, New York, 1995).

Alternatively, the peptides can also be prepared and stored in a salt form, as described above. Various salt forms of the peptides may also be formed or interchanged by any of the various methods known in the art, e.g., by using various ion exchange chromatography methods. Cationic counter ions that may be used in the compositions include, but are not limited to, amines, such as ammonium ions, metal ions, especially monovalent, divalent, or trivalent ions of alkali metals including sodium, potassium, lithium, cesium; alkaline earth metals including calcium, magnesium, barium; transition metals such as iron, manganese, zinc, cadmium, molybdenum; other metals like aluminum; and possible combinations of these. Anionic counter ions that may be used in the compositions described below include chloride, fluoride, acetate, trifluoroacetate, phosphate, sulfate, carbonate, citrate, ascorbate, sorbate, glutarate, ketoglutarate, and possible combinations of these.

The peptides as defined herein can also be prepared using recombinant DNA technology methods.

Peptides according to the invention may also be prepared commercially by companies providing peptide synthesis as a service (e.g., BACHEM Bioscience, Inc., King of Prussia, Pa.; AnaSpec, Inc., San Jose, Calif.). Automated peptide synthesis machines, such as manufactured by Perkin-Elmer Applied Biosystems, also are available.

As detailed above, in specific embodiments the composition of the present disclosure comprises at least one of pharmaceutically acceptable additives, carriers, diluents and excipients.

Pharmaceutical compositions and formulations disclosed herein include those suitable for oral, rectal, nasal, or parenteral (including subcutaneous, intramuscular, intraperitoneal (IP), intravenous (IV) and intradermal) administration.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds (in the present case the peptides of the present disclosure and the at least one additional antiviral therapeutic agent) in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

The disclosed pharmaceutical compositions generally comprise a buffering agent, an agent which adjusts the osmolarity thereof, and optionally, one or more pharmaceutically acceptable additives, carriers, diluents and excipients as known in the art. Supplementary active ingredients can also be incorporated into the compositions.

By the term "pharmaceutically acceptable additives carriers, diluents and excipients" as used herein is meant any and all solvents, dispersion media, coatings, antibacterial and antifungal agents and the like. The use of such media and agents for pharmaceutical active compounds is well known in the art, except for any conventional medium or agent that is incompatible with the active compound.

The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

The presently disclosed pharmaceutical compositions can be conveniently presented in unit dosage form, which can be prepared according to conventional techniques well known in the pharmaceutical industry. Such techniques include bringing into association the active ingredients with the pharmaceutical additive(s), carrier(s) or excipient(s). In general formulations are prepared by uniformly and intimately bringing into association the active ingredients with liquid carriers or finely divided solid carriers or both, and then, if necessary, shaping the product.

Compositions according to the present disclosure can formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome-containing formulations.

The nature, availability and sources, and the administration of all such compounds including the effective amounts necessary to produce desirable effects in a subject are well known in the art and need not be further described herein. The preparation of pharmaceutical compositions is well known to the skilled man of the art and has been described in many articles and textbooks, see e.g., Remington's Pharmaceutical Sciences, Gennaro A. R. ed., Mack Publishing Co., Easton, Pa., 1990, and especially pp. 1521-1712 therein.

The pharmaceutical compositions of the present disclosure can be administered and dosed in accordance with good medical practice. Various methods of administration may be used for delivering the peptides as herein defined or the compositions of the invention to a subject in need. Peptides or composition comprising thereof may be delivered parenterally, e.g. by intravenous (i.v.), intramuscular (i.m.), intraperitoneal (i.p.) or subcutaneous (s.c.) injections or orally (in liquid form or prepared as dosage unit forms like capsules, pills, lozenges, etc.). In order to be effective therapeutically, peptides or composition comprising thereof should be prepared in a way that would enable their stability in the system following injection or oral administration.

In particular embodiments the at least one isolated peptide or composition comprising the same or said at least one additional antiviral agent is administered to said subject by a route selected from the group consisting of intravenous, intramuscular or intraperitoneal administration, intrathecal or subcutaneous injection, oral, intrarectal, intranasal, ocular and topical administration.

The disclosed peptides and additional antiviral agent and their pharmaceutical compositions can be administered also via other routes, depending upon whether local or systemic treatment is desired and upon the area to be treated. Thus, administration can also be topical (including ophthalmic and to mucous membranes including vaginal and rectal delivery), pulmonary, e.g., by inhalation or insufflation of powders or aerosols, including by nebulizer As used herein the term "about" is to be understood as ±10% of the specified value.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Peptides. Peptides were synthesized using fluoronylmethoxycarbonyl chemistry, cleaved and the side chain deprotected with trifluoroacetic acid. Peptides were >95% pure by high-pressure liquid chromatography; molecular weight was verified by MALDI-TOF mass spectrometry. Peptides were abutted with D-Ala at both termini for greater protease resistance in biological assays and with Cys for surface plasmon resonance [9]. Binding of superantigen toxins into the CD28 homodimer interface is essential for induction of cytokine genes that mediate lethal shock [9; 12]. Superantigens hyperinduce inflammatory cytokines by enhancing the B7-2/CD28 costimulatory receptor interaction [12].

Antibodies. Mouse monoclonal anti-CD28 (MAB342, clone 37407), anti-CD3 (clone UCHT1) [9], goat polyclonal anti-CD28 and anti-B7-2 (R&D Systems), horseradish peroxidase-conjugated goat anti-mouse IgG or donkey anti-goat (KPL) antibodies were used.

Induction of cytokine gene expression. Human PBMC were separated on Ficoll Paque (Amersham), washed twice with 50 ml of RPMI 1640 medium, resuspended at $4\times10^6$ cells $ml^{-1}$ and cultured in this medium supplemented with 2% fetal calf serum, 2 mM glutamine, 10 mM MEM nonspecific amino acids, 100 mM Na-pyruvate, 10 mM Hepes pH 7.2, $5\times10^{-5}$ M 2-mercaptoethanol, 100 U $ml^{-1}$ penicillin, 100 $\mu ml^{-1}$ streptomycin and 5 $\mu g\ ml^{-1}$ nystatin. Induction was done with 0.1 $\mu g\ ml^{-1}$ αCD3, 2.5 $\mu g\ ml^{-1}$ αCD28, or both. Secreted cytokines were quantitated in triplicate with Quantikine ELISA kits (R&D Systems).

Ethics approval. Experiments involving mice were done in the AAALAC-accredited Laboratory Animal Research Center of Utah State University and approved by the Institutional Animal Care and Use Committee.

Influenza virus infection of mice. Female BALB/c mice (18-20 g, n=15 for untreated groups and n=10 for treated groups) (Charles River Laboratories, Wilmington, Mass.) were infected intranasally with 50-130 μl of influenza A virus. The avian influenza A/H5N1 virus (H5N1/A/Duck/MN/1525/81) was provided by Dr. Robert Webster (St. Jude Children's Research Hospital, Memphis Tenn.). It was passaged once in Madin-Darby canine kidney (MDCK) cells and three times in mice [13]. Effect of oral gavage treatment with ZnAL42 and other metallo-ion formulations on influenza A H5N1 and H1N1 virus infections in mice. Antivir. Chem. Chemother. 18, 125-132). H5N1 virus was diluted 1:400 (LD100~$1\times10^5$). The mouse adapted pandemic influenza A/H1N1 virus (H1N1/A/California/04/09) was provided by Dr. Elena Govorkova (St. Jude Children's Research Hospital). The virus was first passaged in MDCK cells and then grown in embryonated chicken eggs, adapted to mice by 9 sequential passages, plaque purified in MDCK cells and amplified in embryonated chicken eggs. The virus was then grown in MDCK cells to prepare viral stocks (Nguyen et al., 2012, Efficacy of combined therapy with amantadine, Oseltamivir, and ribavirin in vivo against susceptible and amantadine-resistant influenza A viruses [14]. Mice were exposed to 3 $LD_{50}$ ($10^{3.39}$ PFU) of H1N1 virus. Survival and histopathology was monitored through day 21.

Treatment and dosing. As negative control served phosphate-buffered saline (PSS), given per os and intraperitoneally. All treatments were for the first five days upon virus infection, with two intraperitoneal half doses injections daily, 8 h apart. Positive controls received Ribavirin intraperitoneally (75 mg/kg per day). Treatment groups received peptide p2TA intraperitoneally at various doses, the viral neuraminidase inhibitor, Oseltamivir (Tamiflu, Roche) at 1 or 3 mg/kg per day per os, or combinations of p2TA and Oseltamivir. For determination of cytokine and chemokine levels in lungs, 5 additional mice were included in each group; on day 6, one lobe of each lung from the necropsy was homogenized in 1 ml of minimal essential medium with 50 μg/ml gentamicin and samples were frozen before triplicate cytokine assays (Quansys BioScience Inc.) at 3 dilutions. Results were converted to pg/gram of lung.

Arterial oxygen determination. Arterial oxygen saturation was determined from day 5 on mice set aside for lung analysis, using a Biox 3800 pulse oximeter (Ohmeda, Louisville, Ohio). The ear probe attachment was used with the probe placed on the thigh of the animal; readings were taken after a 30 s stabilization time [15].

Example 1

Protection from Lethal H5N1 Avian Influenza Infection by CD28 Dimer Interface Peptide As indicated above, current strategies for therapy of H5N1 infection focus mostly on neuraminidase inhibitors such as the FDA-approved antiviral Oseltamivir, yet the virus mutates rapidly to become resistant. Treatments aimed at manipulating the host immune system to interfere and prevent cytokine storm initiated by activation of pro-inflammatory Th1 cells by an antigen derived from a viral pathogen such as H5N1, as well as combination therapy targeting virus and host at the same time, may have greater potential in controlling and preventing cytokine storm associated disorders.

Therefore the inventors examined whether the inhibition of superantigen induced Th1 cell activation by short peptides derived from the dimer interface of human CD28 may reduce or prevent cytokine storm caused by Th1 cytokines, and may thus be used for treatment and prophylaxis of cytokine-storm related disorders.

Using a lethal mouse model of avian influenza infection [16], the present inventors tested whether blocking virus-induced Th1 cytokine storm with a peptide derived from or binding to the dimer interface of CD28 as described herein, can protect the mice from death. To this end, H5N1-infected mice were treated for five days with human CD28 dimer interface peptide p2TA abutted at its two termini with D-Alanine (denoted by SEQ ID NO. 7 and also referred to herein as (D-A)-p2TA-(D-A)). As shown by FIG. 1A, in the untreated control group, mortality was 100%. At the lowest dose tested (0.4 μg), p2TA treatment delayed death, but at a nine-fold higher dose (3.6 μg) it afforded partial protection (30% survival) for as long as monitored, 21 days (FIG. 1A only shows survival up to day 14). The inventors also tested the protective effect of the peptide when mice were treated also with the FDA-approved antiviral drug Oseltamivir applied at a dose too low to yield full protection by itself (also referred to herein as a "suboptimal dose" or "sub-therapeutic dose") and found that the peptide was synergistic with Oseltamivir: even at the lowest dose of p2TA, 100% of the mice treated with the combination survived for 21 days. Oxygen saturation data shown in FIG. 1B, illustrate a significant improvement in lung function for mice treated with p2TA, even at the lowest dose. The peptide alone prevented the progressive decline in this parameter seen for untreated animals.

The dose of Oseltamivir used by the inventors should routinely yield only 10-30% survival but in this experiment it gave 70% survival. These data clearly suggest a therapeutic potential for attenuation of CD28 signaling in H5N1 infection with peptides that block the cytokine storm, alone or in combination with an antiviral drug.

Example 2

Protection from Lethal H1N1 Swine Influenza Infection by the CD28 Dimer Interface Peptide p2TA The antiviral activity of the p2TA peptide against an additional influenza strain, H1N1, was also assessed. Mice were infected intranasally with a lethal dose of pandemic H1N1 influenza A virus (H1N1/A/California/04/09 influenza, 3 LD50) and survival was monitored in infected BALB/c mice (18-20 g, n=15 for the untreated groups (Control) and n=10 for the treated groups). Starting from time 0 on day 0, treatment was performed as described below on days 0-4 post infection, twice daily, 8 hours apart. The peptide p2TA was administered intraperitoneally, at doses of 5 or 10 μg per mouse. The agent Oseltamivir (Osel) was administered per os, at 0.3 mg/kg. The agent ribavirin served as a positive control, administered intraperitoneally at 75 mg/kg.

When administered only from the time of infection through day 4 post infection, the peptide p2TA, which is not an antiviral agent by itself, was able to protect mice at least in part from lethal pandemic H1N1 influenza A virus infection, as demonstrated in FIG. 2A. This protective effect of p2TA was dose-dependent: dosed at 5 μg, the peptide yielded only 10% survival (1/10) over 0% (0/10) in the untreated controls, while at a dose of 10 μg, the peptide yielded 40% survival (4/10) (FIG. 2A).

In these mice, the peptide also yielded a partial recovery from infection-induced weight loss that was also dose-dependent and paralleled the weight recovery seen after day 8 with the antiviral drug Ribavirin that served as positive control (FIG. 3A and FIG. 3B). Interestingly, by day 17, both groups had gained close to 20% in weight (FIG. 3A and FIG. 3B).

Surprisingly, the peptide p2TA was strongly synergistic with the viral neuraminidase inhibitor, Oseltamivir. As demonstrated in FIG. 2B, during an independent, severe infection with pandemic H1N1 influenza A virus, the peptide p2TA at a dose of 10 μg per mouse did not prove protective by itself. A sub-therapeutic dose of Oseltamivir (0.3 mg/kg) yielded only 30% survival. However, the combination of p2TA (at 10 μg per mouse) and Oseltamivir (at 0.3 mg/kg) yielded significantly enhanced survival that reached 80% (8/10) (FIG. 2B).

Further to the results presented in Example 1 above, the ability of p2TA to protect mice from lethal influenza infection extends to a pandemic avian IAV strain (H5N1/Duck/MN/1525/81 influenza, 1:400 diluted, LD100~$1\times10^5$, administered intranasally). As shown in FIG. 2C and FIG. 2D, when administered alone in low doses, the peptide p2TA provided a moderate, dose-dependent prolongation of survival over the untreated control group.

Remarkably, even at the lowest concentration that afforded no protection as evidenced in FIG. 2C and FIG. 2D (0.4 μg per mouse), p2TA significantly improved the arterial oxygen saturation level of the infected mice on day 7, at a time when mortality increased rapidly (FIG. 4A). Thus, p2TA treatment has a positive effect on lung function.

Moreover, at a dose that is too low to provide protection alone, namely 0.4 μg per mouse, p2TA strongly synergized with the agent Oseltamivir given at a sub-therapeutic dose (1 mg/kg) which afforded 50% survival (when administered alone), to yield 100% (10/10) survival from lethal H5N1 IAV infection (FIG. 2D) ($p<0.001$ over Oseltamivir at 1 mg/kg). As demonstrated in FIG. 4B, the peptide p2TA again improved the arterial oxygen saturation level of the infected mice (determined on day 6 of the experiment) and in this respect, too, the peptide was clearly synergistic with Oseltamivir, reaching a level close to that seen with the antiviral drug Ribavirin (serving as positive control).

Remarkably, although p2TA had no protective effect and did not lower mortality from H5N1 viral infection when dosed at 0.4 μg per mouse (FIG. 2D), this dose sufficed to significantly reduce inflammatory cytokine levels in the lungs, observed for IFN-γ, IL-6, IL-1β, IL-1α, and the chemokine monocyte chemoattractant protein-1 (MCP-1), as demonstrated in FIG. 4C. p2TA treatment uniformly inhibited the expression of these inflammatory mediators, yet by contrast, did not significantly reduce the level of the anti-inflammatory cytokine, IL-10 (FIG. 4C and FIG. 4D). Indeed, unlike the induction of IFN-γ, induction of IL-10 does not depend on signaling through CD28 [9]. Thus, p2TA-mediated improvement of lung function as observed in FIG. 4A and FIG. 4B was coupled to a reduction in the inflammatory response in the lungs.

The invention claimed is:

1. A method for the treatment of an influenza Type A viral pathogen infection in a human subject in need of such treatment, said method comprising the step of administering to said subject a therapeutically effective amount of:

(a) an isolated peptide selected from the group consisting of SPMLVAYD (SEQ ID NO: 2) and (D-Ala)-SPMLVAYD-(D-Ala) SEQ ID NO: 7, or pharmaceutically acceptable salts and esters thereof, and (b) at least one antiviral therapeutic agent that is a viral neuraminidase inhibitor, wherein the amount of at least one of (a) and (b) administered is sub-therapeutic.

2. The method of claim 1, wherein said treatment prevents worsening, arrests and/or ameliorates at least one symptom of said viral pathogen infection to said subject or an organ or tissue of said subject, associated with said viral pathogen infection, and/or wherein said symptom is at least one of fever, acute respiratory distress syndrome (ARDS), multiple organ dysfunction syndrome (MODS), systemic inflammatory response syndrome (SIRS), hypotension, tachycardia, dyspnea, ischemia, insufficient tissue perfusion, uncontrollable hemorrhage, multisystem organ failure or severe metabolism dysregulation.

3. The method according to claim 1, wherein said isolated peptide and said at least one antiviral therapeutic agent, are administered to said subject following exposure to said viral pathogen, before or after manifestation of clinical symptoms/damage in said subject.

4. The method of claim 1, wherein said at least one antiviral therapeutic agent is administered to said subject at a suboptimal dose.

5. The method of claim 1, wherein said isolated peptide is administered to said human subject at an amount of from about 0.05 mg to about 0.5 mg peptide/kg body weight of said subject.

6. The method of claim 1, wherein said isolated peptide and said at least one antiviral therapeutic agent are administered to said subject simultaneously, or wherein said isolated peptide and said at least one antiviral therapeutic agent are administered to said subject at different time points, at different intervals between administrations, for different treatment periods, and/or at any order of administration and/or wherein each one of said isolated peptide or composition comprising the same and said antiviral therapeutic agent is administered at one or more identical or different treatment periods of one or more weeks of once daily, once every three days, once every five days or once weekly administrations of each of said isolated peptide and said antiviral agent, wherein said treatment periods are consecutive or are set apart from each other by non-treatment intervals of 1 or several days or 1 or several weeks and or wherein each one of said isolated peptide or composition comprising the same and said antiviral agent is administered to said subject immediately following, or within from about 30 minutes up to about 10 days following exposure to the virus and/or wherein said interval between administration of said isolated peptide and said at least one antiviral therapeutic agent is between about 5 minutes to about 5 hours.

7. The method of claim 1, wherein said viral neuraminidase inhibitor is Oseltamivir or Zanamivir.

8. The method of claim 7, wherein said viral neuraminidase inhibitor is Oseltamivir.

* * * * *